(12) United States Patent
Thurston et al.

(10) Patent No.: US 6,747,144 B1
(45) Date of Patent: Jun. 8, 2004

(54) COLLECTIONS OF COMPOUNDS

(75) Inventors: David Edwin Thurston, Nottingham (GB); Philip Wilson Howard, Nottingham (GB)

(73) Assignee: Spirogen Limited (GB)

( * ) Notice: Subject to any disclaimer, the term of this patent is extended or adjusted under 35 U.S.C. 154(b) by 0 days.

(21) Appl. No.: 09/763,813

(22) PCT Filed: Aug. 27, 1999

(86) PCT No.: PCT/GB99/02839

§ 371 (c)(1),
(2), (4) Date: Feb. 26, 2001

(87) PCT Pub. No.: WO00/12509

PCT Pub. Date: Mar. 9, 2000

(30) Foreign Application Priority Data

Aug. 27, 1998 (GB) ............................................. 9818732

(51) Int. Cl.$^7$ ............................................. C07D 487/04
(52) U.S. Cl. ...................................................... 540/496
(58) Field of Search .......................... 514/220; 540/496

(56) References Cited

U.S. PATENT DOCUMENTS

| | | | |
|---|---|---|---|
| 3,523,941 | A | 8/1970 | Leimgruber et al. |
| 3,524,849 | A | 8/1970 | Batcho et al. |
| 4,185,016 | A | 1/1980 | Takanabe et al. |
| 4,239,683 | A | 12/1980 | Takanabe et al. |
| 5,143,854 | A | 9/1992 | Pirrung et al. |
| 5,545,568 | A | 8/1996 | Ellman et al. |

FOREIGN PATENT DOCUMENTS

| | | |
|---|---|---|
| FR | 2027356 | 12/1969 |
| FR | 2 586 683 D | 3/1987 |
| GB | 1 299 198 D | 12/1972 |
| JP | 57 131 791 | 8/1982 |
| JP | 58 180 487 | 10/1983 |
| WO | WO 92/19620 D | 11/1992 |
| WO | WO 97/01560 D | 1/1997 |

OTHER PUBLICATIONS

Foloppe, M.P. et al., "DNA–binding properties of pyrrolo [2,1–c][1,4]benzodiazephine N10–C11 amidines," *Eur. J. Med. Chem.*, 31, 407–410 (1996).
Kamal, A., et al., "An Efficient Synthesis of Pyrrolo[2,1–c] [1,4] Benzodiazepine Antibiotics via Reductive Cyclization," *Bioorg.Med.Chem.Ltrs*, v.7, No. 14, 1825–1828 (1997).
Kamal, A., et al., Synthesis of Pyrrolo [2,1–c][1,4]–Benzodiazepene Antibiotics: Oxidation of Cyclic Secondary Amine with TPAP, *Tetrahedron*, v. 53, No. 9, 3223–3230 (1997).
Thurston, D.E., "Synthesis of Sequence–selective C8–linked Pyrrolo [2,1–c][1,4] Benzodiazepine DNA Interstrand Cross–linking Agent," *J. Org. Chem.*, 61, 8141–8147 (1996).

Bi, Y. et al., "Building blocks for peptide and carbamate libraries", *Bioorganic & Medicinal Chemistry Letters*, vol. 6, No. 19, 2299–2300 (1996). D.
Abstract No. 72145x, Fujisawa, "Benzodiazepine derivatives", *Chemical Abstracts*, vol. 98, No. 9, 638 (1983).
Abstract No. 139983k, Fujisawa, "Benzodiazepine derivatives", *Chemical Abstracts*, vol. 99, No. 17, 603 (1983).
Leimgruber et al., *J. Am. Chem. Soc.*, 87, 5793–5795 (1965).
Leimgruber et al., *J. Am. Chem. Soc.*, 87, 5791–5793 (1965).
Thurston et al.,, *Chem. Rev.*, 1994, 433–465 (1994).
Hochlowski et al.,, *J. Antibiotics*, 40, 145–148 (1987).
Konishi et al.,, *J. Antibiotics*, 37, 200–206 (1984).
Thurston et al., *Chem. Brit.*, 26, 767–772 (1990).
Bose et al., *Tetrahedron*, 48, 751–758 (1992).
Kunimnoto et al., *J. Antibiotics*, 33, 665–667 (1980).
Takeuchi et al., *J. Antibiotics*, 29, 93–96 (1976).
Tsunakawa, et al., *J. Antibiotics*, 41, 1366–1373 (1988).
Shimizu et al., *J. Antibiotics*, 29, 2492–2503 (1982).

(List continued on next page.)

*Primary Examiner*—Deborah C. Lambkin
*Assistant Examiner*—Sonya Wright
(74) *Attorney, Agent, or Firm*—Michael Best & Friedrich, LLP; Grady J. Frenchick; Charlene L. Yager

(57) ABSTRACT

A compound of formula (I), wherein: $R_2$ and $R_3$ are independently selected from H, R, OH, OR, =O, =CH—R, =$CH_2$, $CH_2$—$CO_2R$, $CH_2$—$CO_2H$, $CH^2$—$SO_2R$, O—$SO_2R$, $CO_2R$, COR and CN, and there is optionally a double bond between C1 and C2 or C2 and C3; $R_6$, $R_7$, $R_8$ and $R_9$ are independently selected from H, R, OH, OR, halo, nitro, amino, $Me_3Sn$; $R_{11}$ is either H or R; Q is S, O or NH; L is a linking group, or a single bond; O is a solid support; or where one or more of $R_2$, $R_3$, $R_6$, $R_7$ and $R_8$ are independently: H—$(T)_n$—X—Y—A— where: X is CO, NH, S or O; T is a combinatorial unit; Y is a divalent group such that HY=R; A is O, S, NH, or a single bond and n is a positive integer (I)

3 Claims, 12 Drawing Sheets

OTHER PUBLICATIONS

Langley and Thurston, *J. Org. Chem.*, 52, 91–97 (1987).
Hara et al., *J. Antibiotics*, 41, 702,704 (1988).
Itoh et al., *J. Antibiotics*, 41, 1281–1284 (1988).
Leber et al., *J. Am. Chem. Soc.*, 110, 2992–2993 (1988).
Arima et al., *J. Antibiotics*, 25, 437–444 (1972).
Kohn, *Antibiotics III*, Springer–Verlag, NY, 3–11 (1975).
Hurley and Needham–VanDevanter, *Acc. Chem. Res.*, 19, 230–237 (1986).
Holmes, C. P. Jones, D. G., "Reagents for Combinatorial Organic Synthesis: Development of a New O–Nitrobenzyl Photolabile Linker for Solid Phase Synthesis", *J. Org. Chem.*, 60, 2318–2319 (1995).
Hauske, J. R., Dorff, P. A., Dorff, P. A., "Solid Phase CBZ Chloride Equivalent. A New Matrix Specific Linker", *Tetrahedron Letters*, 36, 10, 1589–1592 (1995).
Kunz, H., Dombo, B., "Solid Phase Synthesis of Peptide and Glycopeptides on Polymeric Supports with Allylic Anchor Groups", *Angew Chem. Int. Ed. Engl*, 5, 711, (1988).
Garcia–Echeverria, C., "A Base Labile Handle for Solid Phase Organic Chemistry", *Tetrahedron Letters*, 38,52, 8933–8934 (1997).
Albericio, F., Giralt, E., Eritja, R., *Tetrahedron Letters*, 32, 1515 (1991).
Albericio, F., Robles, J., Frenandez–Forner, Y., Palom, C., Celma, E., Pedroso, E., Giralt, E., Eritja, R., *Peptides 1990, Proc. $21_{st}$ Eur. Pept. Symp.*, S134 (1991).
Mullen, D. G., Barany, G., "A New Fluoridolyzable Anchoring Linkage for Orthogonal Solid–Phase Peptide Synthesis: Design, Preparation, and Application of the N–(3 or 4)–[[4–(Hydroxymethyl) phenoxy]–tert–butylphenylsilyl]phenyl Pentanedioic Acid Monoamide (Pbs) Handle", *J. Org. Chem.*, 53, 5240 (1988).
Dressman, D. A., et al., *Tet. Letts.*, 37, 937 (1996).
Schreiber et al., *JACS* 120, 23–29 (1998).
Soth, M. J. and Nowick, J. S. "Unnatural oligomer libraries", *Curr. Opin. Chem. Biol.*, 1, No. 1, 120–129 (1997).
Zuckerman et al., "Discovery of Nanomolecular Ligands for 7–Transmembrane G–Protein–Coupled Receptors from a Diverse N–(Substituted) glycine Peptoid Library", *Journal of Medicinal Chemistry*, 37:2678–85 (1994).
Figliozzi, GMR et al., "Synthesis of N–substituted Glycine Peptoid Libraries" *Methods in Enzymology*, 267: 437–47 (1996).
Simon, R. J. et al., "Peptoids: A Modular Approach to Drug Discovery", *Proc. Natl. Acad. Sci. USA*, 89:9367–71 (1992).
P E Nielson et al., *Science*, 254, 1497 (1991).
M Egholm et al., *Nature*, 565, 566 (1993).
M Egholm et al., *JACS*, 114, 1895 (1992).
S C Brown et al., *Science*, 265, 777 (1994).
K Saha et al., *JOC*, 58, 7827 (1993).
K Burgess et al., "Solid Phase Synthesis of Unnatural Biopolymers Containing Repeating Urea Units" *Agnew Chem. Int. Ed. Engl*, 34, No. 8:907 (1995).
K Burgess et al., "Solid Phase Synthesis of Oligoureas", *Journal of the American Chemical Society*, 119: 1556–64 (1997).
E J Moran et al., "Novel Biopolymers for Drug Discovery. Biopolymers", *Peptide Science, John Wiley and Sons*, 37: 213–19 (1995).

Cho, C Y et al., "An Unnatural Biopolymer", *Science*, 261: 1303–5 (1993).
Paikoff S et al., "The Solid Phase Synthesis of N–Alkylcarbamate Oligomers", *Tetrahedron Letters*, 37, No. 32: 5653–56 (1996).
Althius, T. H. and Hess, H. J., *J. Medicinal Chem.*, 20(1), 146–266 (1977).
Mosmann, *J. Immunological Methods*, 65, 55–63 (1983).
Thurston, D. E., "Advances in the study of Pyrrolo[2,1–c][1,4] benzodiazepine (PBD) Antitumour Antibiotics", *Molecular Aspects of Anticancer Drug–DNA Interaction*, Neidle, S., Waring, M.J., Eds.; Macmillan Press Ltd (1993); vol. 1,54–88.
Berry, J. M. et al., *Tetrahedron Letters*, 41, 6171–6174 (2000).
Baraldi, P. G. et al., *J. Med. Chem.*, 42, 5131–5141 (1999).
Nagasaka, T. et al., *Tetrahedron Letters*, vol. 30, No. 14, 1871–72 (1989).
Fukuyama, T. et al., *Tetrahedron Letters*, vol. 34, No. 16, 2577–2580 (1993).
Wilson, S. et al., *Tetrahedron Letters*, vol. 36, No. 35, 6333–6336 (1995).
Nagasaka, T. et al., *Journal of Organic Chemistry*, vol. 36, No. 20, 6797–6801 (1998).
Guiotto, A. et al., *Bioorganic & Medicinal Chemistry Letters*, vol. 8, No. 21, 3017–3018 (1998).
Baraldi, P. et al., *Bioorganic & Medicinal Chemistry Letters*, vol. 8, No. 21, 3019–3024 (1979).
Gregson, S. et al., *Chemical Communications*, 1999, pp. 797–98.
Chemical Abstract No. 4427a, Umezawa, "Mazethramycins" *Chemical Abstracts*, vol. 90, No. 1, 428 (1979).
Chemical Abstract No. 72145x, Fujisawa, "Benzodiazepine derivatives", *Chemical Abstracts*, vol. 98, No. 9, 638 (1983).
Chemical Abstract No. 171573p, O'Neil, "The synthesis of Functionalized Pyrrolo–[2,1–c][1,4]–Benzodiazepines", *Chemical Abstracts*, vol. 126, No. 13, 618 (1997) and entire article.
Chemical Abstract No. 239940r, Farmer, "DNA binding properties of a new class of linked anthramycin analogs", *Chemical Abstracts*, vol. 114, No. 25, 25 (1991) and entire article.
O'Neil, I. A. et al., "DPPE: A Convenient Replacement for Triphenylphosphine in the Staudinger and Mitsunobu Reactions", *Tetrahedron Letters*, vol. 39, No. 42, 7787–7790 (1998).
Thurston, D. E., et al., "Effect of A–ring modifications on the DNA–binding behavior and cytotoxicity of pyrrolo[2,1–c][1,4]benzodiazepines", *Journal of Medicinal Chemistry*, vol. 42, 1951–1964 (1999).
Thurston, D.E., et al., *Chemical Communications*, 563–565 (1996).
Chemical Abstracts No. 300965y, Bi, Y., et al., *Chemical Abstracts*, vol. 125, No. 23, 1013 (1996).
Courtney, S. M. et al., "A new convenient procedure for the synthesis of pyrrolo[2,1–c][1,4]benzodiazepines", *Tetrahedron Letters*, vol. 34, No. 33, 5327–28 (1993).

Reagents   a: Triphosgene, pyridine, $CH_2Cl_2$; b: pyridine, $CH_2Cl_2$; c: TBTU, DIPEA, DMF; d: $SO_3$.pyridine, TEA, $CH_2Cl_2$, DMSO.

Reagents   a: Triphosgene, pyridine, $CH_2Cl_2$; b: pyridine, $CH_2Cl_2$; c: TBTU, DIPEA, DMF; d: $SO_3$.pyridine, TEA, $CH_2Cl_2$, DMSO.

a: LiBH₄, THF; b: SO3.pyridine, TEA, CH₂Cl₂, DMSO; c: MeOH, SOCl₂, CH(OCH₃)₃; d: (i) Raney Nickel, EtOH, (ii) H₂, Pd-C, EtOH.

In vitro cytotoxicity assay for AG 105 (squares); compound 12 + UVA 2h (circles) and compound 12 + UVA 5h (triangles).

COLLECTIONS OF COMPOUNDS

This application is a 317 of PCT/GB99/02839 filed Aug. 27, 1999.

This invention relates to pyrrolobenzodiazepines, to methods of synthesizing these compounds on solid supports, and to collections of these compounds. This invention further relates to methods for identifying and isolating pyrrolobenzodiazepine compounds with useful and diverse activities from such collections.

BACKGROUND TO THE INVENTION

Compounds having biological activity can be identified by screening diverse collections of compounds (i.e. libraries of compounds) produced through synthetic chemical techniques. Such screening methods include methods wherein the library comprises a plurality of compounds synthesized at specific locations on the surface of a solid support whereby a receptor is appropriately labelled to bind to and identify a compound, e.g., fluorescent or radioactive labels. Correlation of the labelled receptor bound to the support and its location on the support identifies the binding compound (U.S. Pat. No. 5,143,854).

Central to these methods is the screening of a multiplicity of compounds in the library and the ability to identify the structures of the compounds which have a requisite biological activity. In order to facilitate synthesis and identification, the compounds in the library are typically formed on solid supports. Usually each such compound is covalently attached to the support via a cleavable or non-cleavable linking arm. The libraries of compounds can be screened either on the solid support or as cleaved products to identify compounds having good biological activity.

A particular class of compounds which would be useful for inclusion in screening libraries are pyrrolobenzodiazepines (PBDs). PBDs have the ability to recognise and bond to specific sequences of DNA; the most preferred sequence is PuGPu (Purine-Guanine-Purine). The first PBD antitumour antibiotic, anthramycin, was discovered in 1965 (Leimgruber et al., 1965 J. Am. Chem. Soc., 87, 5793–5795; Leimgruber et al., 1965 J. Am. Chem. Soc., 87, 5791–5793). Since then, a number of naturally occurring PBDs have been reported, and over 10 synthetic routes have been developed to a variety of analogues (Thurston et al., 1994 Chem. Rev. 1994, 433–465). Family members include abbeymycin (Hochlowski et al., 1987 J. Antibiotics, 40, 145–148), chicamycin (Konishi et al., 1984 J. Antibiotics, 37, 200–206), DC-81 (Japanese Patent 58–180 487; Thurston et al., 1990, Chem. Brit., 26, 767–772; Bose et al., 1992 Tetrahedron, 48, 751–758), mazethramycin (Kuminoto et al., 1980 J. Antibiotics, 33, 665–667), neothramycins A and B (Takeuchi et al., 1976 J. Antibiotics, 29, 93–96), porothramycin (Tsunakawa et al., 1988 J. Antibiotics, 41, 1366–1373), prothracarcin (Shimizu et al, 1982 J. Antibiotics, 29, 2492–2503; Langley and Thurston, 1987 J. Org. Chem., 52, 91–97), sibanomicin (DC-102) (Hara et al., 1988 J. Antibiotics, 41, 702–704; Itoh et al., 1988 J. Antibiotics, 41, 1281–1284), sibiromycin (Leber et al., 1988 J. Am. Chem. Soc., 110, 2992–2993) and tomamycin (Arima et al., 1972 J. Antibiotics, 25, 437–444).

PBDs are of the general structure:

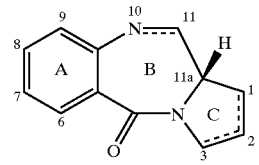

They differ in the number, type and position of substituents, in both their aromatic A rings and pyrrolo C rings, and in the degree of saturation of the C ring. There is either an imine (N=C), a carbinolamine (NH—CH(OH)) or a carbinolamine methyl ether (NH—CH(OMe))at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, 1975 in Antibiotics III. Springer-Verlag, New York, pp. 3–11; Hurley and Needham-VanDevanter, 1986 Acc. Chem. Res., 19, 230–237). Their ability to form an adduct in the minor groove, enables them to interfere with DNA processing, hence their use as antitumour agents.

DISCLOSURE OF THE INVENTION

A first aspect of the present invention relates to compounds of formula (I):

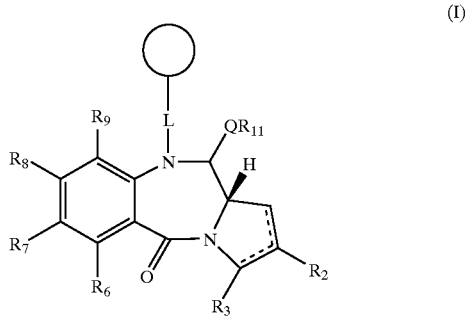

wherein:
$R_2$ and $R_3$ are independently selected from: H, R, OH, OR, =O, =CH-R, =CH$_2$, CH$_2$—CO$_2$R, CH$_2$—CO$_2$H, CH$_2$—SO$_2$R, O—SO$_2$R, CO$_2$R, COR and CN, and there is optionally a double bond between C1 and C2 or C2 and C3;

$R_6$, $R_7$, $R_8$, and $R_9$, are independently selected from H, R, OH, OR, halo, nitro, amino, Me$_3$Sn; or $R_7$ and $R_8$ together from a group —O—(CH$_2$)$_p$—O—, where p is 1 or 2;

$R_{11}$, is either H or R;

Q is S, O or NH;

L is a linking group, or less preferably a single bond;

O is a solid support;

where R is a lower alkyl group having 1 to 10 carbon atoms, or an alkaryl group (i.e. an alkyl group with one or more aryl substituents) preferably of up to 12 carbon atoms, whereof the alkyl group optionally contains one or more carbon-carbon system, or an aryl group, preferably of up to 12 carbon atoms; and is optionally substituted by one or more halo, hydroxy, amino, or nitro groups, and optionally contains one or more hetero atoms, which may form part of, or be, a functional group; and where one or more of $R_2$, $R_3$, $R_6$, $R_7$ and $R_8$ may alternatively be independently X—Y—A—, where X is selected from —COZ', NHZ, SH, or OH, where Z is either H or a nitrogen protecting group, Z' is either OH or an acid protecting group, Y is a divalent group such that HY–R, and A is O, S, NH, or a single bond.

If R is an aryl group and contains a hetero atom, then R is a heterocyclic group. If R is an alkyl chain, and contains a hetero atom, the hetero atom may be located anywhere in the alkyl chain, e.g. —O—$C_2H_5$, —$CH_2$—S—$CH_3$, or may form part of, or be, a functional group, e.g. carbonyl, hydroxy, cyano, ester.

R and HY groups are preferably independently selected from a lower alkyl group having 1 to 10 carbon atoms, or an aralkyl group, preferably of up to 12 carbon atoms, or an aryl group, preferably of up to 12 carbon atoms, optionally substituted by one or more halo, hydroxy, amino, or nitro groups. It is more preferred that R and HY groups are independently selected from a lower alkyl group having 1 to 10 carbon atoms optionally substituted by one or more halo, hydroxy, amino, or nitro groups. It is particularly preferred that R or HY are unsubstituted straight or branched chain alkyl groups, having 1 to 10, preferably 1 to 6, and more preferably 1 to 4, carbon atoms, e.g. methyl, ethyl, propyl, butyl. R may be selected only from methyl and ethyl.

Alternatively, $R_6$, $R_7$, $R_8$ and $R_9$ may preferably be independently selected from R groups with the following structural characteristics:

(i) an optionally substituted phenyl group;
(ii) an optionally substituted ethenyl group;
(iii) an ethenyl group conjugated to an electron sink.

The term 'electron sink' means a moiety-covalently attached to a compound which is capable of reducing electron density in other parts of the compound. Examples of electron sinks include cyano, carbonyl and ester groups.

The term 'nitrogen protecting group' has the meaning usual in synthetic chemistry, particularly synthetic peptide chemistry. It means any group which may be covalently bound to the nitrogen atom of any grouping of the molecule, particularly of the amine grouping, and permits reactions to be carried out upon the molecule containing this protected grouping without its removal. Nevertheless, it is able to be removed from the nitrogen atom without affecting the remainder of the molecule. Suitable amine protecting groups for the present invention include Fmoc (9-fluorenylmethoxycarbonyl), Nvoc (6-nitroveratryloxycarbonyl), Teoc (2-trimethylsilylethyloxycarbonyl), Troc (2,2,2-trichloroethyloxycarbonyl), Boc (t-butyloxycarbonyl), CBZ (benzyloxycarbonyl), Alloc (allyloxycarbonyl) and Psec (2(-phenylsulphonyl)ethyloxycarbonyl). Other suitable groups are described in Protective Groups in Organic Synthesis, T Green and P Wuts, published by Wiley, 1991 which is incorporated herein by reference.

The term 'acid protecting group' has the meaning usual in synthetic chemistry. It means any group which may be reacted with any carboxylic acid moiety of the molecule, and permits reactions to be carried out upon the molecule containing this protected grouping without its removal. Nevertheless, the carboxylic acid moiety is able to be regenerated without affecting the remainder of the molecule. Suitable acid protecting groups include esters, for example methyl ester, and —O—$CH_2$=$CH_2$. Other suitable groups are described in Protective Groups in Organic Synthesis, T Green and P Wuts, published by Wiley, 1991.

It is preferred that in compounds of formula I, if one of $R_2$, $R_3$, $R_6$, $R_7$ and $R_8$ is to be X—Y—A—, then it is either $R_2$ or $R_8$ that is X—Y—A—, and more preferably it is $R_8$ that is X—Y—A—.

In compounds of formula I, Q is preferably O, and $R_{11}$ is preferably H, Me or ET, more preferably H or Me. Independently, $R_6$ is preferably H or R, more preferably H or Me, $R_9$ is preferably H, and $R_7$ is preferably an alkoxy group, and more preferably methoxy or ethoxy. It is further preferred that $R_2$ and $R_3$ are H.

If there is a double bond in the pyrrolo C ring, it is preferably between C2 and C3.

A second aspect of the invention relates to compounds of formula I as defined in the first aspect of the invention except that one or more of $R_2$, $R_3$, $R_6$, $R_7$ and $R_8$ are independently:

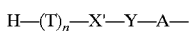

where:

Y and A are as defined in the first aspect of the invention;
X' is CO, NH, S or $O_3$;
T is a combinatorial unit;
and n is a positive integer.

In compounds of formula I according to the second aspect, it is preferred that $R_2$ and/or $R_8$ are independently:

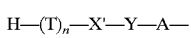

It is preferred that X' is either CO or NH. n may preferably be from 1 to 16, and more preferably from 3 to 14. It is also preferred that it is $R_8$ which is H—$(T)_n$—X'—Y—A—.

A third aspect of the present invention relates to compounds of formula II:

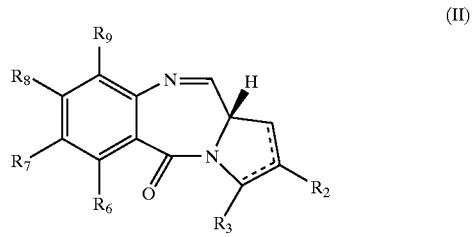

(II)

preferably made from a compound of formula I as described in the first or second aspect of the invention by removing the compound of formula II from the solid support by cleaving the linking group L, where $R_2$, $R_3$, $R_6$, $R_7$, $R_8$, and $R_9$ are as defined in the first or second aspect of the invention.

A fourth aspect of the present invention is a method of making a compound according to the third aspect of the invention from a compound of formula I as described in the first or second aspect of the invention by removing the compound of formula II from the solid support by cleaving the linking group L.

A fifth aspect of the invention relates to a compound of formula II as described in the third aspect of the invention for use in a method of therapy. Conditions which may be treated include gene-based diseases, including neoplastic diseases and, for example Alzheimer's disease, and bacterial, parasitic and viral infections.

In accordance with this aspect of the present invention, the compounds provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosages etc., is within the responsibility of general practitioners and other medical doctors.

A compound may be administered alone or in combination with other treatments, either simultaneously or sequentially dependent upon the condition to be treated.

Pharmaceutical compositions according to the present invention, and for use in accordance with the present invention, may comprise, in addition to the active ingredient, i.e. a compound of formula II, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral., or by injection, e.g. cutaneous, subcutaneous or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solutions, or glycols such as ethylene glycol, propylene glycol or polyethylene glycol may be included. Capsules may include a solid carrier such as gelatin.

For intravenous, cutaneous or subcutaneous injection, or injection at the site of affliction, the active ingredient will be in the form of a parenterally acceptable aqueous solution which is pyrogen-free and which has suitable pH, isotonicity and stability. Those of relevant skill in the art are well able to prepare suitable solutions using, for example, isotonic vehicles such as Sodium Chloride Injection, Ringer's Injection or Lactated Ringer's Injection. Preservatives, stabilisers, buffers, antioxidants and/or other additives may be included, as required.

A sixth aspect of the present invention relates to the use of a compound of formula II as described in the third aspect of the present invention in the preparation of a medicament for the treatment of a gene-based disease or a bacterial, parasitic or viral infection. The preparation of a medicament is described in relation to the fourth aspect of the invention.

In further aspects, the invention provides processes for preparing compounds according to the first and second aspects of the present invention.

Solid Support

The term 'solid support' refers to a material having a rigid or semi-rigid surface which contains or can be derivatized to contain reactive functionality which can serve to covalently link a compound to the surface thereof. Such materials are well known in the art and include, by way of example, silicon dioxide supports containing reactive Si-OH groups, polyacrylamide supports, polystyrene supports, polyethyleneglycol supports, and the like. Such supports will preferably take the form of small beads, pins/crowns, laminar surfaces, pellets or disks. Other conventional forms may be used.

Linker Group

The linking groups preferred for the present application are ones which contain at least one covalent bond which can be readily broken by specific chemical reactions, or other changes (e.g. light or a pH change), thereby providing for liberation of compounds free from the solid support. The chemical reactions employed to break the covalent bond are selected so as to be specific for the desired bond breakage thereby preventing unintended reactions occurring elsewhere in the molecule. The linking group is selected relative to the synthesis of the compounds formed on the solid support so as to prevent premature cleavage of the compound or its precursors from the solid support as well as to avoid interference with any of the procedures employed during synthesis of the compound on the support.

Examples of linking groups are set out below (shown as available form), along with suggested cleavage method(s) for the linking group. These groups are commercially available or have been reported in the literature. After conversion to the appropriate chloroformate, for example by reaction with triphosgene in the presence of pyridine, they can be used to attach to anthranilic acids (for use in providing the protected A-rings of pyrrolobenzodiazepines) via carbamate linkages. Some resins, e.g. p-nitrophenyl carbonate Wang resin may couple to the anthranilic acids without need for intermediate transformation to the chloroformate.

Cleavage Conditions

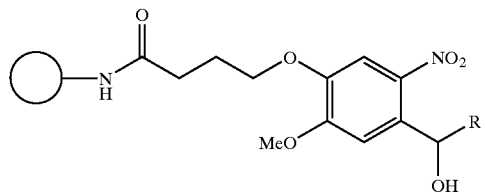

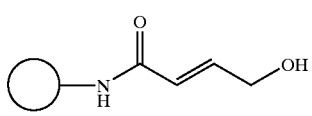

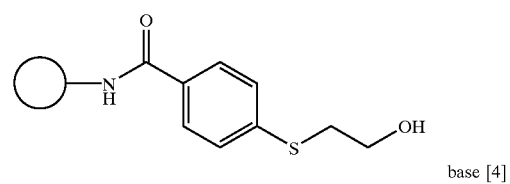

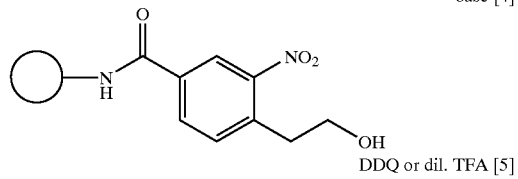

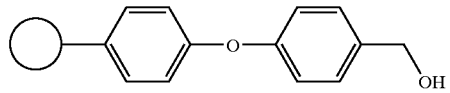

-continued

TBAF [6]

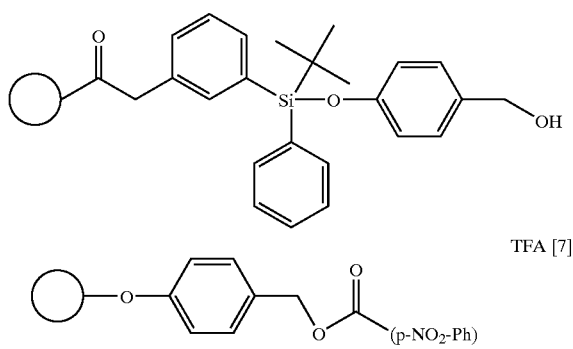

TFA [7]

References

1. Holmes, C. P., Jones, D. G., "Reagents for Combinatorial Organic Synthesis: Development of a New O-Nitrobenzyl Photolabile Linker for Solid Phase Synthesis", *J. Org. Chem.*, 60, 2318–2319 (1995).
2. Hauske, J. R., Dorff, P. A., "Solid Phase CBZ Chloride Equivalent. A New Matrix Specific Linker", *Tetrahedron Letters*, 36, 10, 1589–1592 (1995).
3. Kunz, H., Dombo, B., "Solid Phase Synthesis of Peptide and Glycopeptides on Polymeric Supports with Allylic Anchor Groups", *Angew Chem Int Ed Engl*, 5, 711 (1988).
4. Garcia-Echeverria, C., "A Base Labile Handle for Solid Phase Organic Chemistry", *Tetrahedron Letters*, 38, 52, 8933–8934 (1997).
5. (a) Albericio, F., Giralt, E., Eritja, R., *Tetrahedron Letters*, 32, 1515 (1991).
   (b) Albericio, F., Robles, J., Fernandez-Forner, Y., Palom, C., Celma, E., Pedroso, E., Giralt, E., Eritja, R., Peptides 1990, *Proc 21st Eur. Pept. Symp.*, S134, (1991).
6. Mullen, D. G, Barany, G., "A New Fluoridolyzable Anchoring Linkage for orthogonal Solid-Phase Peptide Synthesis; Design, Preparation, and Application of the N-(3 or 4)-[[4- (Hydroxymethyl)phenoxy]-tert-butylphenylsilyl]phenyl Pentanedioic Acid Monoamide (Pbs) Handle", *J. Org. Chem.*, 53, 5240 (1988).
7. Dressman, D. A., et al., *Tet. Letts.*, 37, 937 (1996). All these documents are incorporated herein by reference.

Combinatorial Unit

The term 'combinatorial unit' means any monomer unit which can be used to build a chain as shown in a compound of formula I as defined in the second aspect of the present invention, or a compound of formula II, when derived from a compound of formula I as defined in the second aspect of the present invention. The chain is usually attached to the PBD core by a joining group through the pro N10 position. Examples of molecules suitable for such chain building are found in Schreiber et al. (JACS, 120, 1998, pp.23–29), which is incorporated herein by reference. An important example of a unit is an amino acid residue. Chains may be synthesised by means of amine-protected amino acids. Fmoc protected amino-acids are available from a number of sources, such as Sigma and NovaBiochem. Both natural and unnatural amino acids can be used, e.g. D- and L-amino acids and heterocyclic amino acids. In particular, heterocyclic amino acids of the type found in the construction of netropsin and distamycin are of interest because of their DNA-recognition properties.

Amine units can be used to make up peptoids: see Soth, M. J. and Nowick, J. S. 1997, Unnatural oligomer libraries, *Curr. Opin, Chem. Biol.* 1, no. 1: 120–129; Zuckermann et al., 1994, Discovery of Nanomolecular Ligands for 7-Transmembrane G-Protein-Coupled Receptors from a Diverse N-(Substituted)glycine Peptoid Library, *Journal of Medicinal Chemistry* 37: 2678–85; Figliozzi, GMR et al., 1996, Synthesis of N-substituted Glycine Peptoid Libraries, *Methods in Enzymology*, 267: 437–47; Simon, R. J. et al., 1992, Peptoids: A Modular Approach to Drug Discovery, *Proc. Natl. Acad. Sci. USA*, 89:9367–71; which documents are incorporated herein by reference.

Other combinatorial units include PNAs: P E Nielsen, et al., *Science*, 1991, 254, 1497; M Egholm, et al., *Nature*, 1993, 365, 566; M Egholm et al., *JACS*, 1992, 114, 1895; S C Brown, et al., *Science*, 1994, 265, 777; 5. K Saha, et al., *JOC*, 1993, 58, 7827; oligoureas: K Burgess, et al., 1995, Solid Phase Synthesis of Unnatural Biopolymers Containing Repeating Urea Units. *Agnew. Chem. Int. Ed. Engl* 34, no. 8:907; K Burgess, et al., 1997, Solid Phase Synthesis of Oligoureas; *Journal of the American Chemical Society* 119: 1556–64; and oligocarbamates: E J Moran et al., 1995, Novel Biopolymers for Drug Discovery. *Biopolymers (Peptide Science)*; John Wiley and Sons 37: 213–19; Cho C Y et al., 1993, An Unnatural Biopolymer. *Science* 261: 1303–5; Paikoff S F et al., 1996, The Solid Phase Synthesis of N-Alkylcarbamate Oligomers. *Tetrahedron Letters* 37, no. 32: 5653–56. All these documents are incorporated herein by reference.

A type of combinatorial unit of particular relevance to the present invention is one based on the pyrrolobenzodiazepine structures; these are of general formulae IIIa and IIIb:

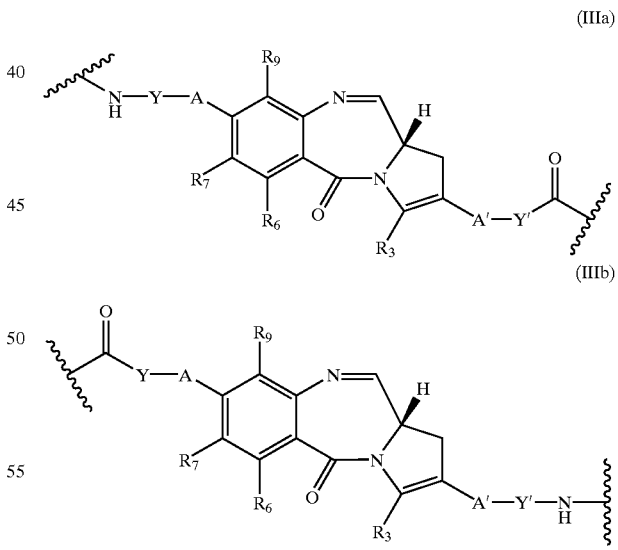

wherein $R_3$, $R_6$, $R_7$ $R_9$, A and Y are as defined in the first aspect of the invention, A' and Y' are independently selected from the possible groups for A and Y respectively. In order for such combinatorial units to be added to the combinatorial chain, they may be added in their protected form as shown in general formulae IIIc and IIId:

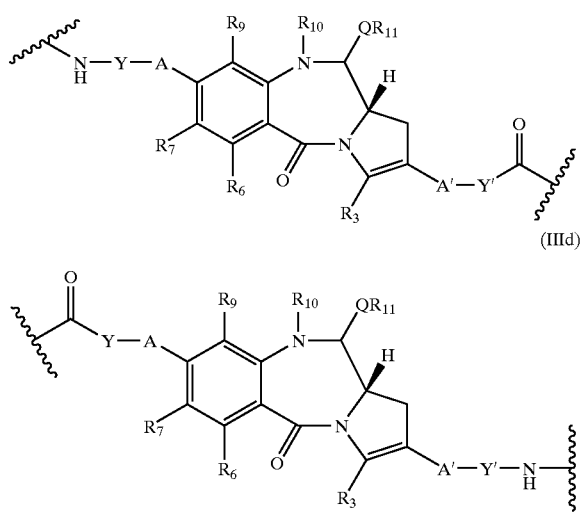

where $R_3$, $R_6$, $R_7$, $R_9$, A, Y, A' and Y' are as defined above, Q and $R_{11}$ are as defined in the first aspect of the invention, and $R_{10}$ is a nitrogen protecting group. It is possible that the combinatorial units may remain in their protected form until the compound has been cleaved from the solid support, or until any other components of the compound have been deprotected.

The present invention relates to libraries, or collections, of compounds all of which are represented by a single one of the formulae I or II. The diversity of the compounds in a library may reflect the presence of compounds differing in the identities of one or more of $R_2$, $R_3$, $R_6$, $R_7$, $R_9$, $R_{11}$ and Q and/or in the identities of the combinatorial units T (when present). The number of members in the library depends on the number of variants, and the number of possibilities for each variant. For example, if it is the combinatorial units which are varied, and there are 3 combinatorial units, with 3 possibilities for each unit, the library will have 27 compounds. 4 combinatorial units and 5 possibilities for each unit gives a library of 625 compounds. If for instance there is a chain of 5 combinatorial units with 17 possibilities for each unit, the total number of members in the library would be 1.4 million. A library may therefore comprise more than 1 000, 5 000, 10 000, 100 000 or a million compounds, which may be arranged as described below.

In the case of free compounds (formula II), the individual compounds are preferably in discrete volumes of solvents, e.g. in tubes or wells. In the case of bound compounds (formula I) the individual compounds are preferably bound at discrete locations, e.g. on respective pins/crowns or beads. The library of compounds may be provided on a plate which is of a suitable size for the library, or may be on a number of plates of a standard size, e.g. 96 well plates. If the number of members of the library is large, it is preferable that each well on a plate contains a number of related compounds from the library, e.g. from 10 to 100. One possibility for this type of grouping of compounds is where only a subset of the combinatorial units, or substituents, are known and the remainder are randomised; this arrangement is useful in iterative screening processes(see below). The library may be presented in other forms that are well-known.

A further aspect of the present invention is a method of preparing a collection, or library of compounds as discussed above. If the diversity of the library is in the combinatorial units, then the library may be synthesised by the stepwise addition of protected combinatorial units to a PBD core, each step being interposed by a deprotection step. Such a method is exemplified later. If the diversity of the library is in the substituent groups, the library may be synthesised by carrying out the same synthetic methods on a variety of starting materials or key intermediates, which already possess the necessary substituent patterns.

The present invention also relates to a method of screening the compounds of formula II to discover biologically active compounds. The screening can be to assess the binding interaction with nucleic acids, e.g. DNA or RNA, or proteins, or to assess the affect of the compounds against protein-protein or nucleic acid-protein interactions, e.g. transcription factor DP-1 with E2F-1, or estrogen response element (ERE) with human estrogen receptor (a 66 kd protein which functions as a hormone-activated transcription factor, the sequence of which is published in the art and is generally available). The screening can be carried out by bringing the target macromolecules into contact with individual compounds or the arrays or libraries of individual compounds described above, and selecting those compounds, or wells with mixtures of compounds, which show the strongest effect.

This effect may simply be the cytotoxicity of the compounds in question against cells or the binding of the compounds to nucleic acids. In the case of protein-protein or nucleic acid-protein interactions, the effect may be the disruption of the interaction studied.

Protein-protein interactions can be measured in a number of ways, e.g. FRET (fluorescence resonance energy transfer) which involves labelling one of the proteins with a fluorescent donor moiety and the other with an acceptor which is capable of absorbing the emission from the donor; the fluorescence signal of the donor will be altered depending on the interaction between the two proteins. Another method of measuring protein-protein interactions is by enzymatic labelling, using, for example, horseradish peroxidase.

The screening process may undergo several iterations by selecting the most active compounds, or groups of compounds, tested in each iteration; this is particularly useful when testing arrays of wells which include mixtures of related compounds. Furthermore, if the wells contain compounds for which only a subset of the combinatorial units, or substituents, are known, but the rest are randomised, subsequent iterations can be carried out by synthesising compounds possessing the selected known (and successful) combinatorial unit, or substituent, pattern, but with further specified combinatorial units, or substituents, replacing the previously randomised combinatorial units, or substituents, adjacent the already known pattern; the remaining combinatorial units, or substituents, are randomised as in the previous iteration. This iterative method enables the identification of active members of large libraries without the need to isolate every member of the library.

A further feature of this aspect is formulation of a selected compound or selected compounds with pharmaceutically acceptable carriers or diluents.

A further aspect of the present invention relates to the use of compounds of formula II in target validation. Target validation is the disruption of an identified DNA sequence to ascertain the function of the sequence, and a compound of formula II can be used to selectively bind an identified sequence, and thus disrupt its function.

Compounds of formula II can also be used in functional genomics to ascertain the biological function of individual genes, by blocking this biological action. This is a further aspect of the invention.

Synthesis Methods

A key step in a preferred route to compounds of formula I is a cyclisation procedure to produce the B-ring, involving generation of an aldehyde (or functional equivalent thereof) at what will be the 11-position, and attack thereon by the pro-10-nitrogen:

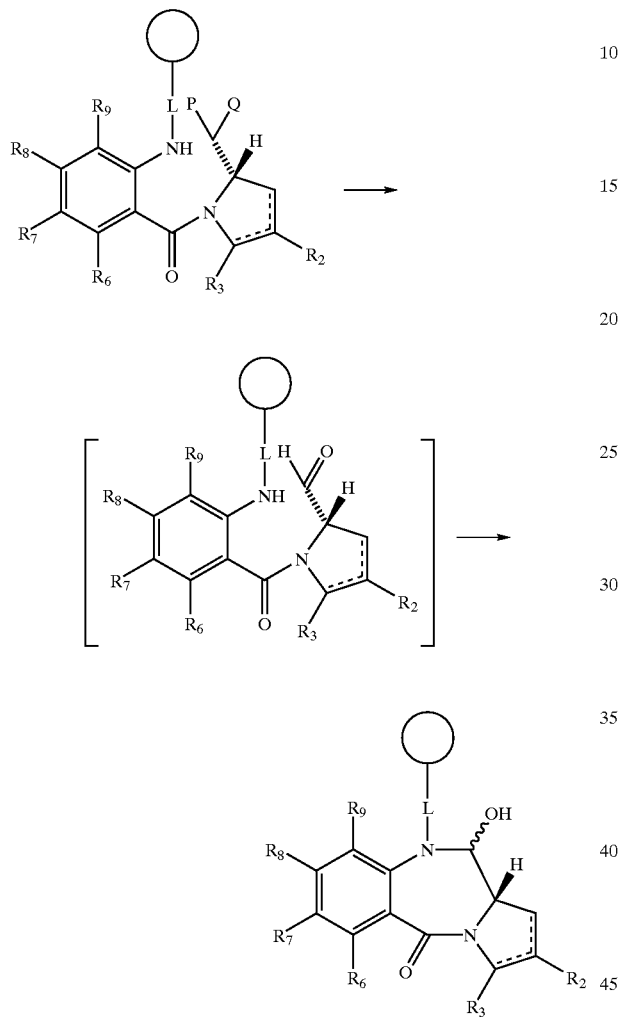

The "masked aldehyde" —CPQ may be an acetal or thioacetal, which may be cyclic, in which case the cyclisation involves unmasking. Alternatively, it may be an alcohol —CHOH, in which case the reaction involves oxidation, e.g. by means of TPAP or DMSO (Swern oxidation).

The masked aldehyde compound can be produced by condensing a corresponding 2-substituted pyrrolidine with a 2-nitrobenzoic acid:

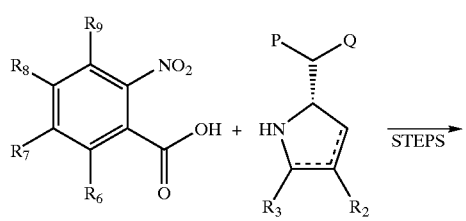

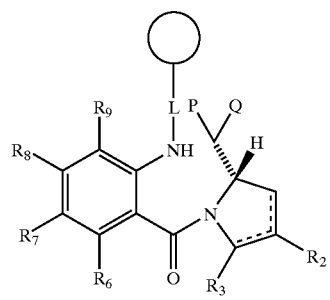

The nitro group can then be reduced to —$NH_2$ and reacted with a suitable linking group attached to a solid support, e.g. a chloroformate, which thereby links the structure to the solid support.

A process involving the oxidation-cyclization procedure is illustrated in scheme 1 (an alternative type of cyclisation will be described later with reference to scheme 2).

Scheme 1

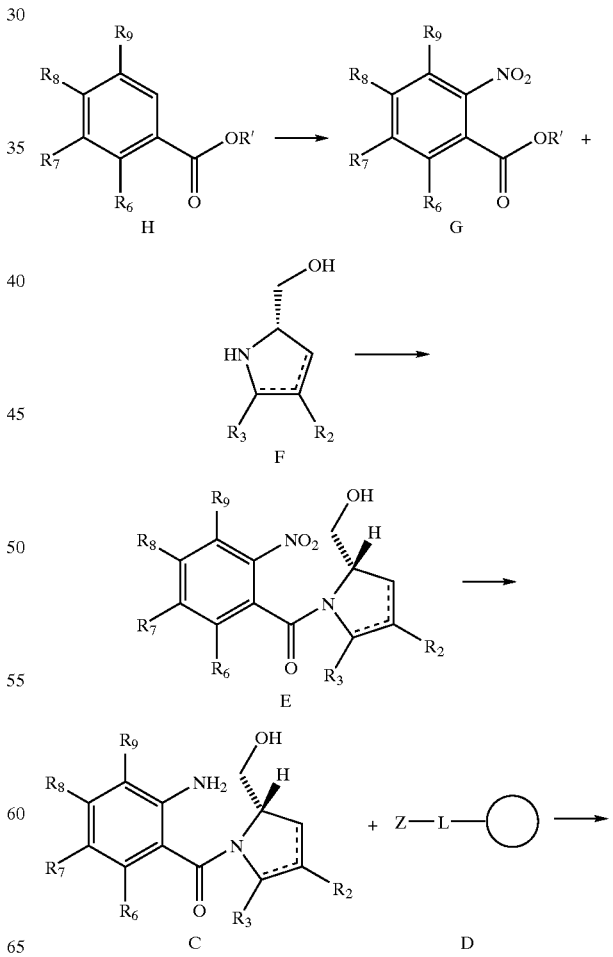

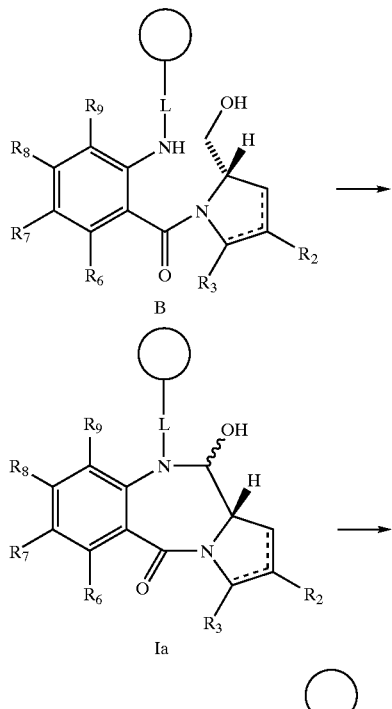

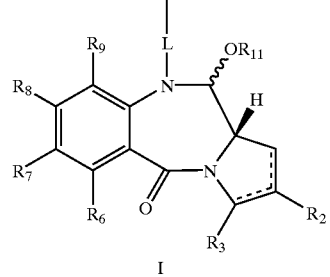

If $R_{11}$ is other than hydrogen, the compound of formula I, may be prepared by direct etherification of the alcohol Ia. Compounds with Q=S can be prepared by treatment of the corresponding alcohol Ia with $R_{11}SH$, and a catalyst (usually a Lewis Acid such as $Al_2O_3$). For compounds where Q=NH, these can be prepared by reacting an amine, $R_{11}NH$, e.g. $C_3H_7NH$ with the corresponding alcohol Ia normally with a catalyst, such as a Lewis Acid.

Exposure of the alcohol B to tetrapropylammonium perruthenate (TPAP)/N-methylmorpholine -oxide (NMO) over A4 sieves results in oxidation accompanied by spontaneous B-ring closure to afford the desired product. The TPAP/NMO oxidation procedure is found to be particularly convenient for small scale reactions while the use of DMSO-based oxidation methods, particularly Swern oxidation, proves superior for larger scale work (e.g. >1 g).

The uncyclized alcohol B may be prepared by the reaction of the amino alcohol C, generally in solution, with the linking group L attached to a solid support D. The linking group is preferably terminated with a chloroformate or acid chloride functionality. This reaction is generally carried out in the presence of a base such as pyridine (preferably 2 equivalents) at a low temperature (e.g. at 0° C.).

The key amino alcohol C may be prepared by reduction of the corresponding nitro compound E, by choosing a method which will leave the rest of the molecule intact. For example, treatment of E with tin (II) chloride in a suitable solvent, e.g. refluxing methanol, generally affords, after the removal of the tin salts, the desired product C in high yield.

Exposure of E to hydrazine/Raney nickel avoids the production of tin salts and may result in a higher yield of C, although this method is less compatible with the range of possible C and A-ring substituents. For instance, if there is C-ring unsaturation (either in the ring itself, or in $R_2$ or $R_3$), this technique may be unsuitable.

The nitro compound of formula E may be prepared by coupling the appropriate o-nitrobenzoyl chloride to a compound of formula F, e.g. in the presence of $K_2CO_3$ at $-25°$ C. under a $N_2$ atmosphere. Compounds of formula F can be readily prepared, for example by olefination of the ketone derived from L-trans-hydroxy proline. The ketone intermediate can also be exploited by conversion to the enol triflate for use in palladium-mediated coupling reactions.

The o-nitrobenzoyl chloride is synthesised from the o-nitrobenzoic acid (or alkyl ester, after hydrolysis) of formula G, which itself is prepared from the vanillic acid (or alkyl ester) derivative H. Many of these are commercially available and some are disclosed in Althuis, T. H. and Hess, H. J., *J. Medicinal Chem.*, 20(1), 146–266 (1977).

Alternative Cyclisation (Scheme 2)

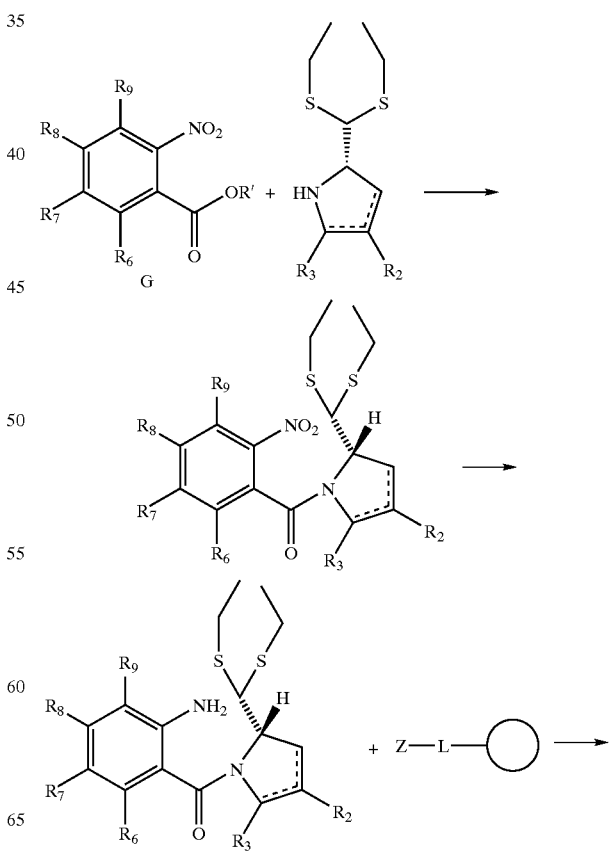

-continued

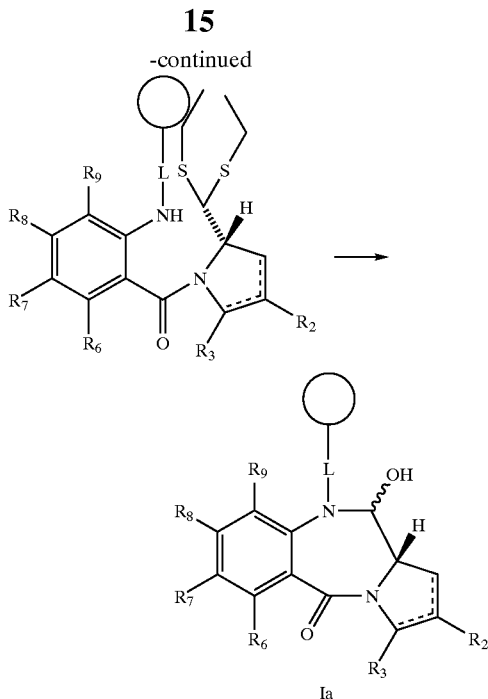

Ia

In scheme 1, the final or penultimate step was an oxidative cyclisation. An alternative route, using thioacetal coupling, is shown in scheme 2. Mercury-mediated unmasking causes cyclisation to the desired compound (Ia)

The thioacetal compound may be prepared as shown in scheme 2: the thioacetal protected C-ring [prepared via a literature method: Langley, D. R., & Thurston, D. E., *J. Organic Chemistry*, 52, 91–97 (1987)] is coupled to the o-nitrobenzoic acid (or alkyl ester) G using a literature procedure. The resulting nitro compound cannot be reduced by hydrogenation because of the thioacetal group, so the tin(II) chloride method is used to afford the amine. This is then N-protected, e.g., by reaction with a chloroformate or acid chloride, such as p-nitrobenzylchloroformate.

Acetal containing C-rings can be used as an alternative in this type of route with deprotection including other methods, including the use of Lewis Acid conditions (see example 3).

In the above synthesis schemes, the derivatisation of the A-ring is shown as being complete before the compounds are attached to the solid support. This is preferred if the substituents are groups such as alkoxy or nitro. On the other hand, substituent groups such as alkyl or alkenyl could be added to the A-ring after the coupling of the compound to the solid support. This may be achieved by $R_6$, $R_7$, $R_8$, or $R_9$ being easily replaceable groups, such as a halogen atom.

An alternative synthesis route (as in Examples 3 and 4—FIGS. 4 and 5) is to attach the component which will form the A ring to the solid support at the pro N10 position, before joining the component which will form the C ring.

Embodiments of the present invention will now be described by way of example with reference to the accompanying drawings in which.

GENERAL METHODS

Figure 1:
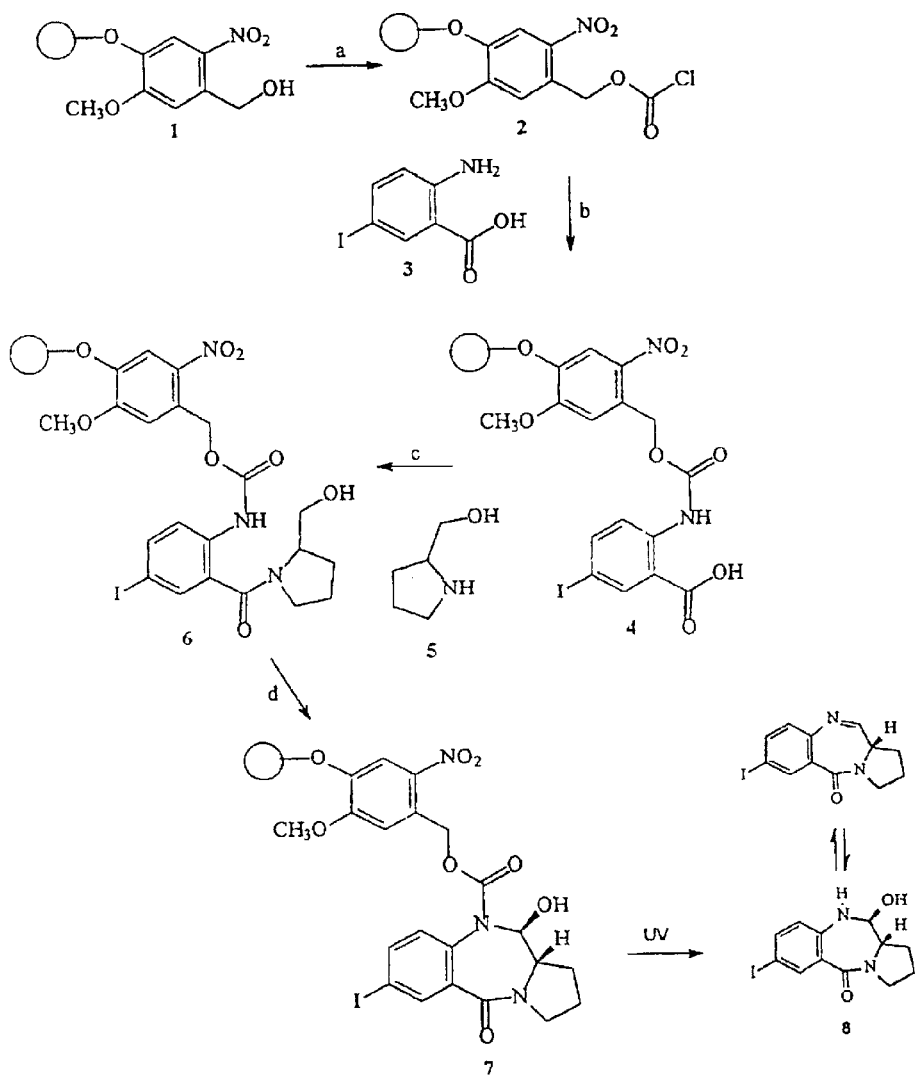
FIG. 1 is a synthesis scheme for a compound according to the invention.

Melting points (mp) were determined on a Gallenkamp P1384 digital melting point apparatus and are uncorrected. Infrared (IR) spectra were recorded using a Perkin-Elmer 297 spectrophotometer. $^1$H- and $^{13}$C- NMR spectra were recorded on a Jeol GSX 270 MHZ FT-NMR spectrometer operating at 20° C. +/−1° C. Chemical shifts are reported in parts per million (δ) downfield from tetramethylsilane (TMS). Spin multiplicities are described as: s (singlet), bs (broad singlet), d (doublet), dd (doublet of doublets), t (triplet), q (quartet), p (pentuplet) or m (multiplet). Mass spectra (MS) were recorded using a Jeol JMS-DX 303 GC Mass Spectrometer (EI mode: 70 eV, source 117–147° C.). Accurate molecular masses (HRMS) were determined by peak matching using perfluorokerosene (PFK) as an internal mass marker, and FAB mass spectra were obtained from a glycerol/thioglycerol/trifluoroacetic acid (1:1:0.1) matrix with a source temperature of 180° C. Optical rotations at the Na-D line were obtained at ambient temperature using a Perkin-Elmer 141 Polarimeter. Analytical results were generally within +/−0.2% of the theoretical values. Flash chromatography was performed using Aldrich flash chromatography "Silica Gel-60" (E. Merck, 230–400 mesh). Thin-layer chromatography (TLC) was performed using $GF_{254}$ silica gel (with fluorescent indicator) on glass plates. All solvents and reagents, unless otherwise stated, were supplied by the Aldrich Chemical Company Ltd. and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 60–80° C.

Overall Synthetic Strategy for Examples 1 and 2

The pyrrolobenzodiazepine products 8 and 13 were obtained in solution by exposure to light at 365 nm; light at this wavelength promotes the conversion of the photolabile linker into a nitroso aldehyde, in the process liberating the PBD from the resin. In addition to this photolabile linker, other fluoride, mild acid, mild base or palladium (0)/nucleophile labile linkers may also be used in the construction of PBD libraries.

The bead bound PBDs 7 and 12 (FIGS. 1 and 2 respectively) were prepared by oxidation of the primary-alcohol-bearing resins 6 and 11 with $SO_3$.Pyridine complex in DMSO. Other oxidizing systems such as TPAP/NMO, the Dess Martin reagent, and oxalyl chloride/DMSO (Swern oxidation) are also effective (see example 5). The primary alcohol resins 6 and 11 were obtained from the coupling of the bead bound anthranilic acids 4 and 10 to pyrrolidine methanol 5. Alternatively, coupling (2S, 4R)-2-t-butyldimethylsilyloxymethyl-4-hydroxy proline to the bead-bound anthranilic acid offers the opportunity of elaborating the PBD C-ring at the pro-C2-position on bead via, for example, olefination. Finally, the bead bound anthranilic acids 4 and 10 were obtained by coupling the commercially available anthranilic acids (over 40 anthranilic acids are commercially available) to the o-nitrobenzylchloroformate resin 2 which was in turn obtained from the commercially available resin 1 by treatment with triphosgene in the presence of dry pyridine.

EXAMPLE 1

Synthesis of the Resin-Bound C7-Iodo-PBD Carbinolamine (7) (FIG. 1)

Ortho-nitro Benzyl Chloroformate Resin (2)

Hydroxymethyl-photolinker NovaSyn TG resin 1 (0.2 g, 0.24 mol/g loading) was placed in a vessel, fitted with a sinter. Dichlororethane $CH_2Cl_2$ (3 mL) was added and the vessel shaken for 30 minutes. The suspension was then cooled to 0° C. before adding triphosgene (0.15 g, 0.5 mmol) in $CH_2Cl_2$ and pyridine (40 μL, 0.5 mmol), and the vessel allowed to shake at room temperature for 16 hours. The chloroformate resin 2 was collected by filtration and rinsed with $CH_2Cl_2$ (2×5 mL) and MeOH (2×5 mL), and dried in vacuo. IR (reflectance, $cm^{-1}$): 1700 (C=O).

Attaching Iodinated A-Ring to Form Resin (4)

Dichloromethane $CH_2Cl_2$ (5 mL) was added to resin 2 (0.048 mmol) and the vessel was allowed to shake for 30 minutes. The suspension was then cooled to 0° C. and a solution of iodoanthranilic acid 3 (0.13 g, 0.48 mmol) and pyridine (40 μl) in NMP (2 mL) was added, and the vessel was allowed to shake at room temperature for 16 hours. Resin A was then collected by filtration, rinsed with $CH_2Cl_2$ (2×5 mL), NMP (2×5 mL) and MeOH (2×5 mL), and dried in vacuo. HPLC analysis after release of iodoanthranilic acid by irradiation indicated that 58% of available sites had been carbanoylated. IR (reflectance, $cm^{-1}$): 1750–1650 (CONH).

Attaching Pyrrolo C-Ring to From Resin (6)

Dimethyl formamide DMF (5 mL) was added to resin 4 (0.036 mmol) and the vessel allowed to shake for 30 minutes. Pyrrolidine methanol 5 (40 μl, 0.36 mmol), TBTU (0.12 g, 0.36 mmol) in DMF (1 mL) and DIPEA (65 μl, 0.36 mmol) were added, and the vessel allowed to shake at room temperature for 16 hours. Resin 6 was collected by filtration, rinsed with $CH_2Cl_2$ (2×5 mL) and MeOH (2×5 mL), and dried in vacuo. IR (reflectance, $cm^{-1}$): 1650–1600 (C=O).

B-Ring Cyclisation to Form Bead-Bound Carbinolamine (7)

Dichloromethane $CH_2Cl_2$ (0.5 mL) was added to resin 6 (0.024 mmol) and the vessel allowed to shake for 30 minutes. The suspension was then cooled to -10° C., and triethylamine (10 μl, 0.072 mmol) and sulphur trioxide.pyridine complex (0.012 g, 0.072 mmol) in DMSO (0.25 mL) added. Shaking was continued for 1 hour at 10° C, and the resin 7 was then collected by filtration, rinsed with $CH_2Cl_2$ (2×5 mL) and MeOH (2×5 mL), and dried in vacuo.

The resulting compound 7 may be cleaved from the solid support by UV light of a wavelength of 365 nm to form a compound of formula 8.

Further Synthesis Steps

The compound of formula 7 may serve as a starting point for the synthesis of a wide variety of other compounds. The iodine at the C8 position can be reacted with a boronic acid with Pd $(PPh_3)_4$ as a catalyst in modified Suzuki reaction. An alternative synthesis route is to stanylate the C8 position by reacting the compound of formula 8 with $Me_6Sn_2$, with Pd $(PPh_3)_4$ as a catalyst. The stanylated compound is capable of coupling with acrylates (i.e. the Heck reaction), iodo- and bromo-arenes (i.e. the Suzuki reaction) and haloalkenes (i.e. the Stille reaction).

EXAMPLE 2

Figure 2:
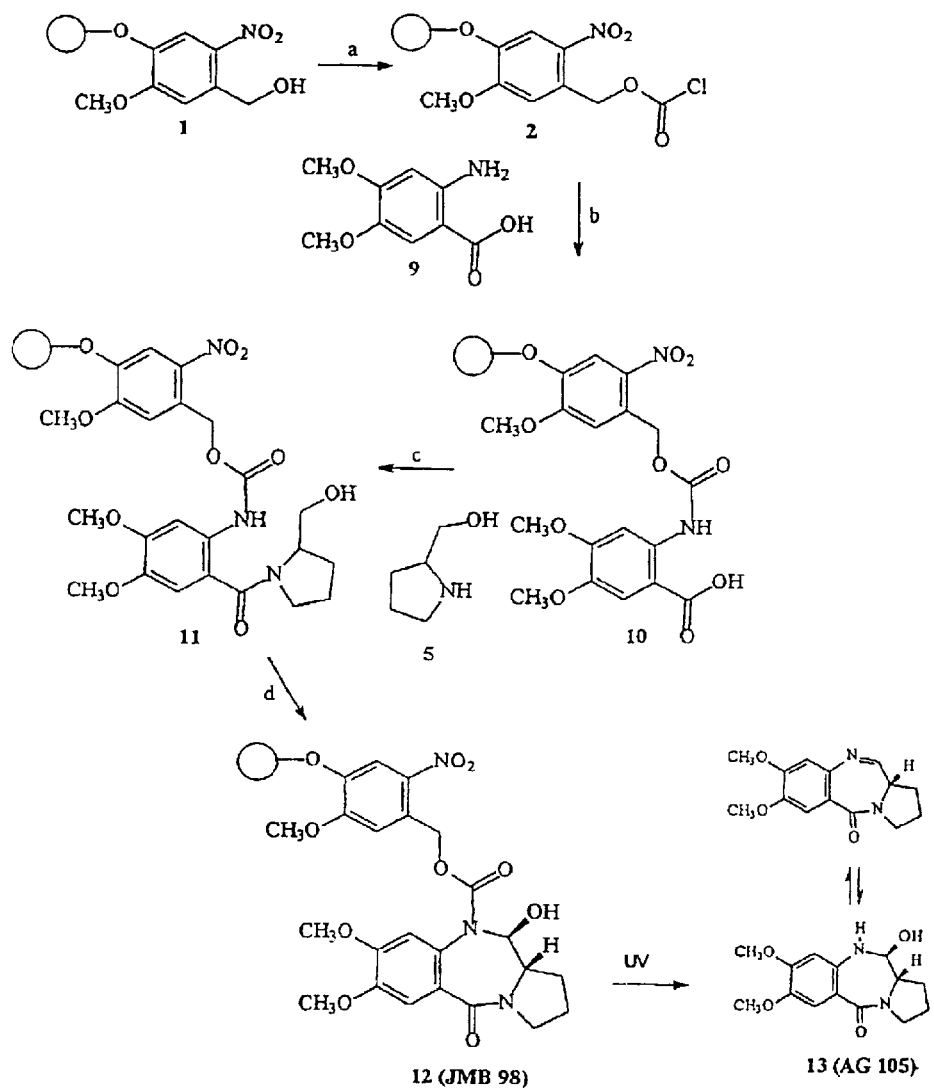
FIG. 2 is a synthesis scheme for another compound according to the invention.

Synthesis of Resin-bound 7,8-Dimethoxy PBD (12) (FIG. 2)

Attaching Dimethoxy A-Ring to Form Resin (10)

Dichloromethane $CH_2Cl_2$ (2 mL) was added to the choloroformate resin 2 (0.05 mmol) (prepared as in Example 1) and the vessel allowed to shake for 30 minutes. The suspension was cooled to 0° C., a solution of 4,5-dimethoxyanthranilic acid 9 (0.05 g, 0.25 mmol) and pyridine (20 μL) in NMP (2 mL) added, and the vessel allowed to shake at room temperature for 16 hours. The resin 10 was collected by filtration, and then rinsed with $CH_2Cl_2$ (2×5 mL), NMP (2×5 mL) and MeOH (2×5 mL). The entire procedure was repeated twice and the resin was then dried in vacuo. IR (reflectance, $cm^{-1}$): 1750–1650 (CONH).

Attaching Pyrrolo C-Ring to Form Resin (11)

Dimethyl formamide DMF (5 mL) was added to resin 10 (0.05 mmol) and the vessel allowed to shake for 30 minutes. Pyrrolidine methanol 5 (0.025 g, 0.25 mmol), TBTU (0.08 g, 0.25 mmol) in DMF (1 mL) and DIPEA (45 μL, 0.25 mmol) were added, and the vessel allowed to shake at room temperature for 16 hours. The resin 11 was collected by filtration, and rinsed with DMF (2×5 mL), NMP (2×5 mL) and $CH_2Cl_2$ (2×5 mL). The entire procedure was repeated twice, and the resin then dried in vacuo. IR (reflectance, $cm^{-1}$): 1700–1600 (C=O).

B-Ring Cyclisation to Form Bead-Bound Carbinolamine (12)

Dichloromethane $CH_2Cl_2$ (1 mL) was added to resin 11 (0.05 mmol) and the vessel allowed to shake for 30 minutes. The suspension was cooled to -10° C, and triethylamine (20 μL, 0.15 mmol) and sulphur trioxide.pyridine complex (0.024 g, 0.15 mmol) in DMSO (0.5 mL) were added. The suspension was then allowed to warm to room temperature, and the vessel was left to shake for 2 hours. The resin 12 was collected by filtration and rinsed with $CH_2Cl_2$ (2×5 mL,) and MeOH (2×5 mL). The entire procedure was repeated twice and the resin then dried in vacuo.

EXAMPLE 3

Figure 3:
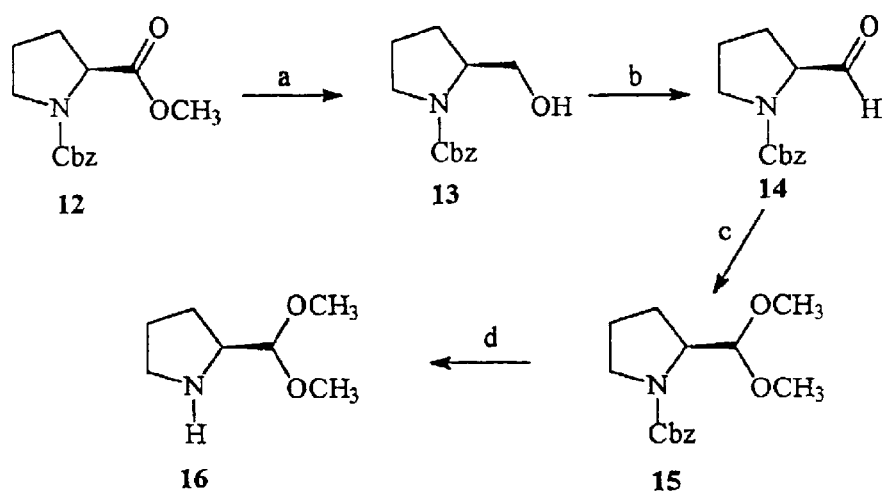
FIG. 3 is a synthesis scheme for an intermediate in the synthesis of a compound according to the invention.
Figure 4:
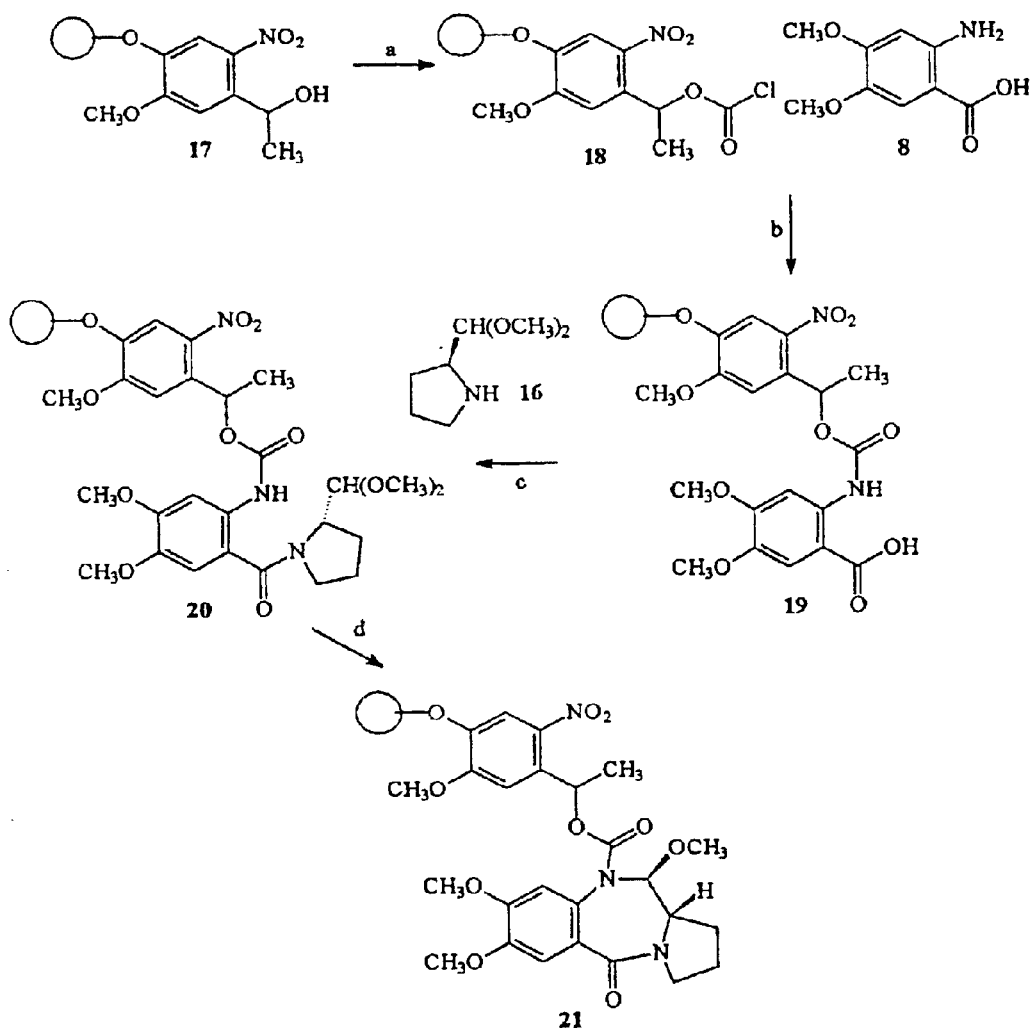
FIGS. 4 and 5 are synthesis schemes for further compounds according to the invention.

Alternative Synthesis of Resin-bound 7,8-Dimethoxy PBD (21) (FIGS. 3 & 4)

Overall Synthetic Strategy

The on-bead oxidation step employed in the previous approaches can be avoided by coupling an anthranilic acid loaded resin to the dimethyl acetal 16 derived from proline (FIG. 4). In this approach, unmasking of the dimethyl acetal protected aldehyde leads to spontaneous B-ring closure. Thus, exposure of the acetal 20 to a palladium catalyst $(Pd(CH_3CN)_2Cl_2)$ leads to the formation of the cyclized compound 21. The acetal 20 was derived from the anthranilic acid resin 19 and the acetal 16, which were coupled together under standard conditions. The acetal 16 was obtained from the Cbz protected compound 15 (FIG. 3) by hydrogenation; 15 was in turn prepared by acetalisation of the aldehyde 14. Swern oxidation of the primary alcohol 13 afforded the aldehyde 14, the primary alcohol was prepared by a lithium tetrahydroborate reduction of the commercially available Cbz protected proline ester ester 12.

(2S-N-(benzoxycarbonyl)-2-hydroxymethylproline (13)

Lithium tetrahydroborate (2.6 g, 0.12 mol) was added portionwise to a solution of N-Carbobenzyloxy-L-proline methyl ester 12 (21 g, 0.08 mol) in THF (500 mL) at 0° C. The reaction mixture was allowed to stir at room temperature for 48 hours. The solution was then cooled to 0° C. and ice water (150 mL) was added to quench excess lithium tetrahydroborate. The resulting suspension was adjusted to pH 4.0 with aqueous HCl (1.0 N) and extracted with $Et_2O$ (250 mL). The organic phase was separated and washed with $H_2O$ (3×100 mL), brine (2×100 mL), dried ($MgSO_4$) and concentrated to give alcohol 13 as a pale yellow oil (18.6 g, 99%). $^1H$ NMR (270 $MH_z$, $CDCl_3$) δ 2.1–1.77 (m, 4H); 3.76–3.35 (m, 4H); 4.1–3.77 (m, 1H); 5.14 (2×s, 2H); 7.38–7.28 (m, 5H). CIMS 236 ($M^+$).

(2S)-N-benzoxycarbonyl)pyrrolidine-2-carboxaldehyde (14)

A solution of triethylamine (32 mL, 0.23 mol) and $SO_3$.pyridine complex (37 g, 0.23 mol) in DMSO (210 mL) a solution of alcohol 13 (18 g, 0.077 mol) in $CH_2Cl_2$ (250 mL) at −10° C., under a nitrogen atmosphere. The reaction mixture was allowed to warm to room temperature and stirred for 30 minutes and then poured into ice water (200 mL) and extracted with $Et_2O$. The organic phase was washed with aqueous HCl (1.0 N, 3×150 mL), $H_2O$ (3×150 mL), brine (2×150 mL), dried ($MgSO_4$) and concentrated to give a yellow oil. The crude material was purified by flash column chromatography (EtOAc) to give aldehyde 14 as a colourless oil (12.6 g, 71%). $^1H$ NMR (270 $MH_z$, $CDCl_3$) δ 2.16–1.8 (m, 4H); 3.66–3.5 (m, 2H); 4.22–4.17 (m, 1H); 5.22–5.13 (m, 2H); 7.37–7.3 (m, 5H); 9.59 (2×s, 1H). CIMS 234 ($M^+$+1).

(2S)-N-(benzoxycarbonyl)pyrrolidine-2-carboxaldehyde dimethyl acetal (15)

Thionyl chloride (5.5 mL) was added to a solution of aldehyde 14 (11 g, 0.047 mol) and trimethyl orthoformate (36 mL, 0.33 mol) in MeOH (55 mL) at 0° C. The reaction mixture was heated at 60° C. for 2 hours. The solution was allowed to cool to room temperature, and treated with excess solid $Ha_2CO_3$ and diluted with $Et_2O$ (60 mL) The suspension was filtered to remove insoluble inorganics and resultant filtrate was concentrated in vacuo and the redissolved in EtOAc. The organic solution was washed with saturated aqueous $NaHCO_3$ (3×50 mL), brine (2×50 mL), dried ($MgSO_4$) and concentrated to give the acetal 15 as a yellow liquid (12.5 g, 95%). $^1H$ NMR (270 $MH_z$, $CDCl_3$) δ 2.16–17 (m, 4H); 3.64–3.33 (m, 4.02–3.91 (br. m, 1H); 4.4 and 4.6 (2×br. s, 1H); 4.4 and 4.6 (2×br. s, 1H); 5.17–5.1 (m, 2H); 7.47–7.28 (m, 5H).

Pyrrolidine-2-carboxaldehyde Dimethyl Acetal (16)

A solution of acetal 15 (5.8 9, 0.02 mol) in EtOH (50 mL) was allowed to stir for 16 hours at room temperature over Raney nickel (0.2 g), in order to remove the trace amounts of sulphur impurities prior to hydrogenation. Excess nickel was removed by filtration through Celite.

10% palladium on carbon (580 mg) was added to the alcoholic solution which was subjected to hydrogenation under pressure (c. 50 psi). After 16 hours, the reaction mixture was filtered through Celite and the pad washed with EtOAc, the combined organic solutions were concentrated to give the secondary amine 16 as a pale green liquid (2.9 g, 100%). $^1H$ NMR (270 $MH_z$, $CDCl_3$) δ 1.93–1.59 (m, 4H); 3.1–2.92 (m, 2H); 3.4–3.3 (d, J=6.9 Hz, 1H); 3.41 (2×s, 6H); 3.53 (br. s, 1H); 4.2 (d, J=6.8 Hz, 1H).

Synthesis of Resin-bound Methyl Ester 21 (FIG. 4)

A suspension of hydroxyethyl-photolinker NovaSyn TG resin 17 (0.114 g, 0.24 mmol/g loading) in $CH_2Cl_2$ (1 mL) in a vessel fitted with a sinter was shaken for 30 minutes. The suspension was cooled to 0° C., before addition of a solution of triphosgene (0.04 g, 0.14 mmol) and pyridine (11 mL, 0.14 mmol) in $CH_2Cl_2$ (0.5 mL). The vessel was allowed to shake at room temperature for 16 hours. The resin 18 was filtered and rinsed with $CH_2Cl_2$ (2×2 mL) NMP (2×2 mL) and $CH_2Cl_2$ (2×2 mL). This procedure was repeated twice and the resin was then dried in vacuo.

A suspension of resin 18 (0.027 mmol) in $CH_2Cl_2$ (1 mL) was allowed to shake for 30 mins. The suspension was cooled to 0° C. and a solution of 4,5-dimethoxy-anthranilic acid 9 (0.03 g, 0.14 mmol) and pyridine (10 mb) in NMP (0.5 mL) was added. The vessel was allowed to shake at room temperature for 16 hours.

Resin 19 was filtered and rinsed with $CH_2Cl_2$ (2×2 mL), NMP (2×2 mL) and MeOH (2×2 mL). The procedure was repeated twice and then the resin was dried in vacuo.

A suspension of resin 19 (0.027 mmol) in DMF (1 mL) was allowed to shake for 30 minutes. To this suspension was added the acetal 16 (20 mg, 0.14 mmol), TBTU (43 mg, 0.14 mmol) and DIPEA (25 mL, 0.144 mmol) in DMF (0.5 mL). The vessel was allowed to shake at room temperature for 2 hours after which time the resin 20 was filtered and rinsed with DMF (2×1 mL), $CH_2Cl_2$ (2×1 mL) and MeOH (2×1 mL). The procedure was repeated twice and then the resin was dried in vacuo.

A suspension of resin 20 (0.027 mmol) in acetone (0.5 mL) was allowed to shake for 30 minutes. To this suspension was added $PdCl_2(CH_3CN)_2$ (7 mg, 0.027 mmol) in acetone (0.4 mL) and the vessel was allowed to shake at room temperature for 2 hours. The resulting resin 21 was filtered and rinsed with acetone (2×1 mL), $CH_2Cl_2$ (2×1 mL) and MeOH (2×1 mL). The procedure was repeated twice and then the resin was dried in vacuo.

EXAMPLE 4

Figure 5:
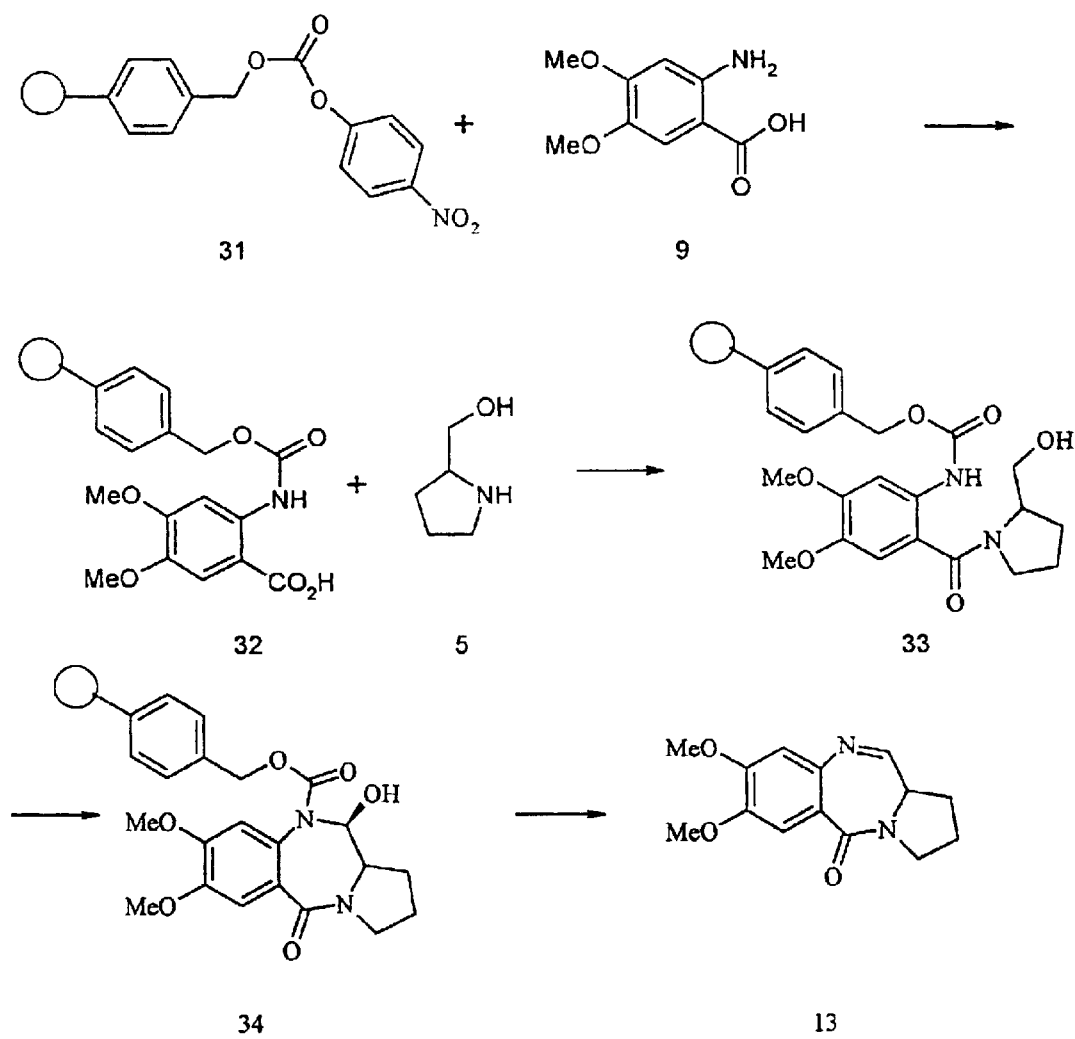

Further Alternative Synthesis of 7,8-Dimethoxy PBD (13) (FIG. 5)

Overall Synthetic Strategy

This synthesis used the on-bead oxidation step of example 1 and 2 to obtain the resin-bound PBD 34, but using the Dess Martin reagent and Swern oxidation. The resin used to bind the required anthranilic acid 31 is p-nitrophenyl carbonate Wang resin, which can directly couple the anthranilic acid without the need for interactive transformation to the chloroformate and thus eliminating a process step.

Synthesis Route

A suspension of p-nitrophenyl carbamate Wang resin 31 (1 g, 0.93 mmol/g loading) in $CH_2Cl_2$/DMF (2:1, 10 mL)

was shaken for 30 minutes. A solution of dimethoxyanthranilic acid 9 (0.92 g, 4.7 mmol), HOBt (0.37 g, 2.8 mmol) and DIPEA (0.97 mL, 5.5 mmol) in $CH_2Cl_2$/DMF (2:1, 20 mL) was added to the swollen resin. The vessel was allowed to shake at room temperature for 6 hours. Resin 32 was filtered and rinsed with DMF (2×10 mL), $CH_2Cl_2$ (2×10 mL), MeOH (2×10 mL), $Et_3O$ (10 mL) and dried in vacuo.

A suspension of resin 32 (0.93 mmol) in DMF (10 mL) was allowed to shake for 30 minutes. A solution of pyrrolidine methanol 5 (0.47 g, 4.7 mmol), TBTU (1.5 g, 4.7 mmol) and DIPEA (0.81 mL, 4.7 mmol) in DMF (10 mL) was added to the swollen resin. The vessel was allowed to shake at room temperature for 6 hours. Resin 33 was filtered and rinsed with DMF (2×10 mL), $CH_2Cl_2$ (2×10 mL), MeOH (2×10 mL), $Et_2O$ (10 mL) and dried in vacuo. This entire procedure was repeated once.

A suspension of resin 33 (0.93 mmol) in $CH_2Cl_2$ (10 mL) was allowed to shake for 30min. A solution of Dess Martin periodinane (1.97 g, 4.7 mmol) in $CH_2Cl_2$ (20 mL) was added to the swollen resin. The vessel was allowed to shake at room temperature for 2 hours. Resin 34 was filtered and rinsed with $CH_2Cl_2$ (2×10 mL), MeOH (2×10 mL), $Et_2O$ (10 mL) and dried in vacuo.

A suspension of resin 34 (0.93 mmol) in TFA/$CH_2Cl_2$ (20 mL) was allowed to shake for 2 hours. The resultant red solution was decanted off and the procedure was repeated on the remaining resin, to ensure complete cleavage. The combined organic solution was diluted with water (20 mL) and carefully neutralised to pH 7.0 by the addition of solid sodium bicarbonate. The organic phase was separated and washed with $H_2O$ (3×20 mL), brine (2×20 mL), dried ($MgSO_4$) and concentrated to give a red film. The crude material was purified by flash column chromatography (silica gel, 1% MeOH/$CHCl_3$) to give imine 13, as a beige solid (142 mg, 59%).

$^1$H NMR (270 MHz, $CDCl_3$) δ 2.4–1.26 (m, 6H), 3.9–3.82 (m, 1H), 3.96 and 3.93 (2×s, 6H), 6.81 (s, 1H), 7.52 (s, 1H), 7.69–7.67 (d, J=4.2 Hz, 1H); $^{13}$C NMR (68.7 MHz, $CDCl_3$) δ 24.2, 29.4, 38.7, 46.7, 53.7, 56.4, 109.4, 111.3, 120.3, 140.7, 147.5, 151.3, 162.5, 164.6.

Alternative Oxidation Method

A suspension of resin 33 (0.6 mmol) in $CH_2Cl_2$ (10 ML) was allowed to shake for 30 min. A solution of $SO_2$-pyridine complex (0.96 g, 6 mmol) and triethylamine (5 mL, 0.036 mol) in DMSO (5 mL) was added to the swollen resin. The vessel was allowed to shake at room temperature for 3 hours. Resin 34 was filtered and rinsed with $CH_2Cl_2$ (2×10 ML), MeOH (2×10 mL), $Et_2O$ (10 mL) and dried in vacuo.

A suspension of resin 34 (0.6 mmol) in TFA/$CH_2Cl_2$ (1:1, 20 mL) was allowed to shake for 3 hours. The resultant red solution was decanted off and was diluted with water (20 mL) and carefully neutralised to pH 7.0 by the addition of solid sodium bicarbonate. The organic phase was separated and washed with $H_2O$ (3×20 mL), brine (2×20 mL), dried ($MgSO_4$) and concentrated to give a luminous yellow oil. The crude material was purified by flash column chromatography (silica gel, 5% MeOH/$CHCl_3$) to give imine 13, as a yellow film (60 mg, 38%) (NHR as above).

EXAMPLE 5

Synthesis of Three Resin Bound PBDs (52, 53, 54)

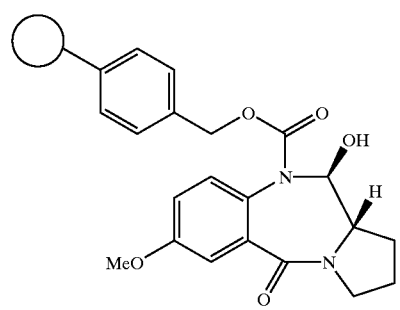

52

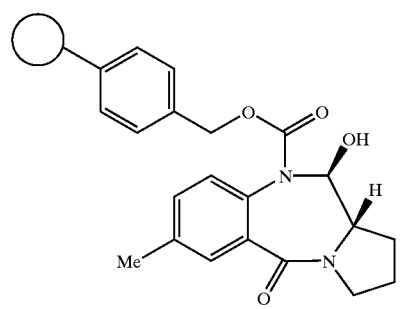

53

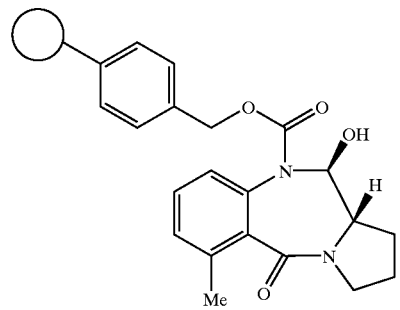

54

Compounds 52 and 53 were synthesised in the same way as example 4, using the alternative oxidation method (Swern) starting from the appropriate anthranilic acids (52: 5-methoxyanthranilic acid; 53: 5-methylanthranailic acid). Compound 54 was synthesieed in the same way as example 4 using the first oxidation method (Dess Martin) starting from 6-methylanthranilic acid. The EIMS (M+H)$^+$ results for the compounds, after cleavage from the solid support, were: 52–230; 53–214; 54–215.

EXAMPLE 6

Cleavage of PBDs From Beads

HPLC Method

Assays of the PBDs synthesised in example 2 were carried out on a reversed-phase 25 cm×4.6mm (inside diameter) C4 (Nucleosil™; 5 mm bead size) column protected with a Delta-Pak™ C4, 300 Å Guard pre-column. Elution was carried out using a mobile phase consisting of MeOH/$H_2O$ (1:1) at a flow rate of 1 mL/min. A Waters 490E multiwavelength detector was used. Peak identification was accomplished by reference to an authentic sample of compound 13 synthesized "off-bead".

| Conditions | |
|---|---|
| INJECTION VOLUME: | 20 μL |
| FLOW RATE: | 1 mL/min |
| MOBILE PHASE: | 50% METHANOL/50% WATER |
| STATIONARY PHASE: | C4, 5 μm (REVERSED PHASE) |
| COLUMN: | WATERS 300 Å |
| DETECTOR: | 254 nm |
| RUN TIME: | 20 mins |

Figure 6:
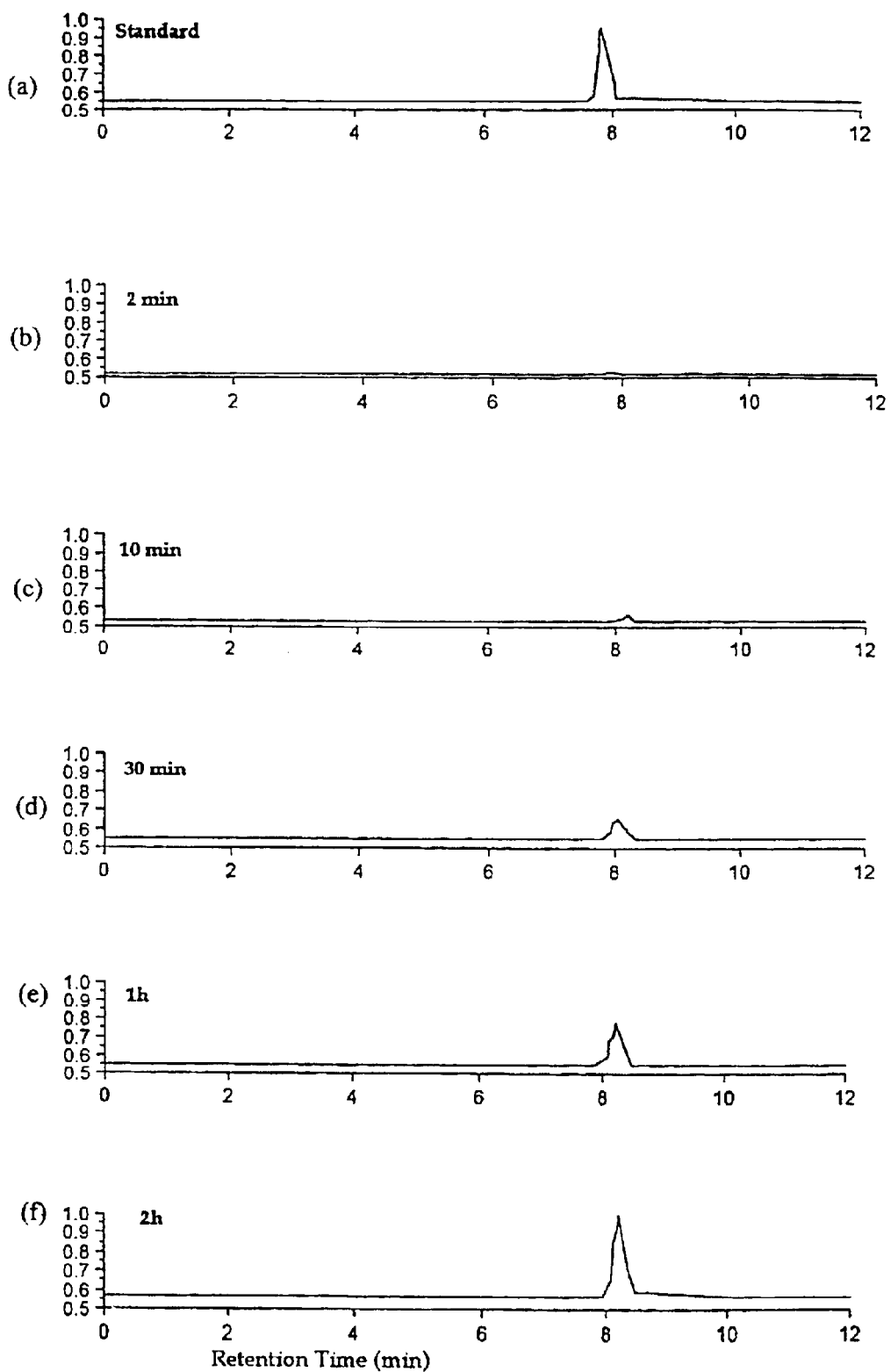
FIG. 6 is an HPLC time course for cleavage of the compound made by the scheme shown in FIG. 2.
Figure 7:
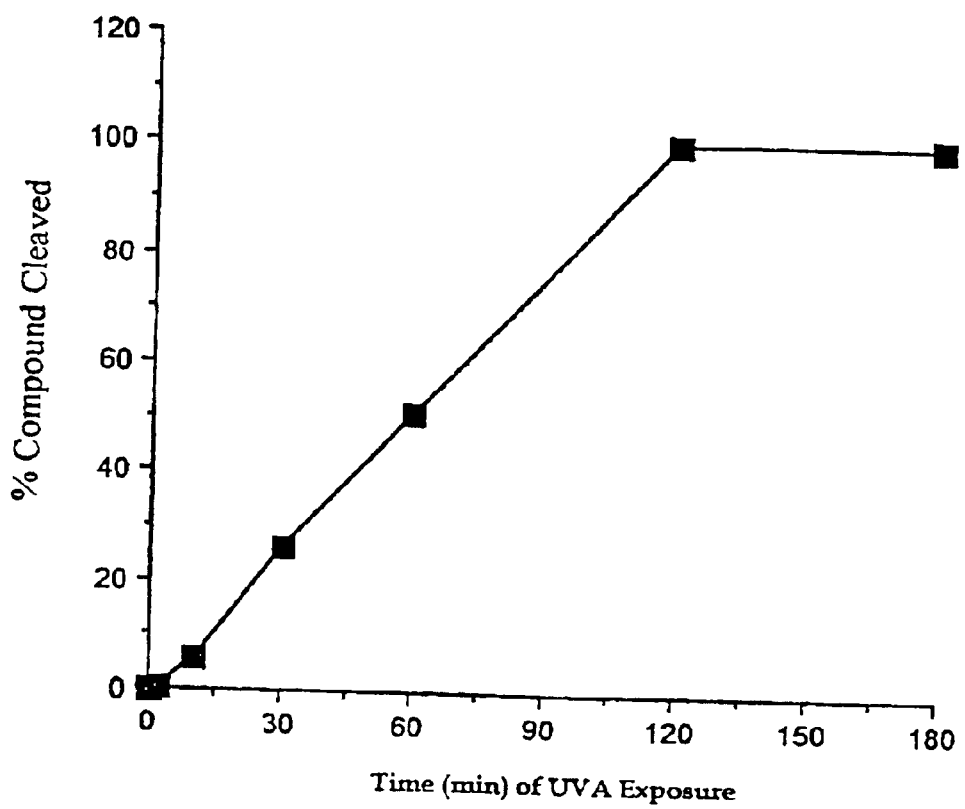
FIG. 7 is a graph which illustrates the results shown in FIG. 6.

Cleavage of the PBD from beads following UVA irradiation was monitored by HPLC. The resin-bound compound 12 (JMB 98) at a concentration of 1 mM in DMF was UVA irradiated. At appropriate time intervals, samples were centrifuged to pellet the beads and the amount of free PBD released into the supernatant determined by HPLC. After photolysis of resin 12, carbinolamine 13 was the only species produced as determined by reference to an authentic sample of compound 13 synthesised "off bead". Typical HPLC traces of authentic 13 and of the PBD cleaved from resin 12 with increasing irradiation times are shown in FIG. 6, and the percentage cleavage with time shown in FIG. 7. Cleavage occured linearly with time, and complete cleavage was achieved by 2 hours under the conditions used. HPLC studies indicated that 77% of the sites on the beads had reacted.

In Vitro Cytotoxicity Assay

MTT Assay Method

The ability of agents to inhibit the growth of chronic human histiocytic leukaemia U937 cells or human chronic myeloid leukaemia K562 cells in culture was measured using the MTT assay (Mosmann, 1983). This assay is based on the ability of viable cells to reduce a yellow soluble tetrazolium salt, 3-(4,5-dimethylthiazolyl)-2,5-diphenyltetrazolium bromide (MTT; Sigma Chemical Co.), to an insoluble purple formazan precipitate. Cells at a density of 5×104 cells/mL were continuously incubated with the test compounds at a final concentration of 0.3 μM. Aliquots of each of the compounds of the 27-member library were either left without UVA:(365 nm) exposure or were exposed to UVA (365 nm) for 2 hours prior to their addition to the cell suspension. Following drug treatment, the cells were transferred to 96-well microtitre plates, $10^4$ cells per well, 8 wells per sample. The plates were incubated at 37° C. in a humidified atmosphere containing 5% $CO_2$. Following incubation of the plates for 4 days (to allow control cells to increase in number 10-fold), 20 μL of a 5 mg/mL solution of MTT in phosphate-buffered saline was added to each well and the plates further incubated for 5 hours. The plates were then centrifuged for 5 minutes at 300 g, and the bulk of the medium removed from the cell pellet, leaving 10–20 μL per well. DMSO (200 μL) was added to each well, and the samples agitated to ensure complete mixing. The optical density was then read at a wavelength of 550 nm using a Titertek Multiscan ELISA plate reader and the dose-response curve constructed. The $IC_{50}$ value was read as the dose required to reduce the final optical density to 50% of the control value.

Results

Figure 8:
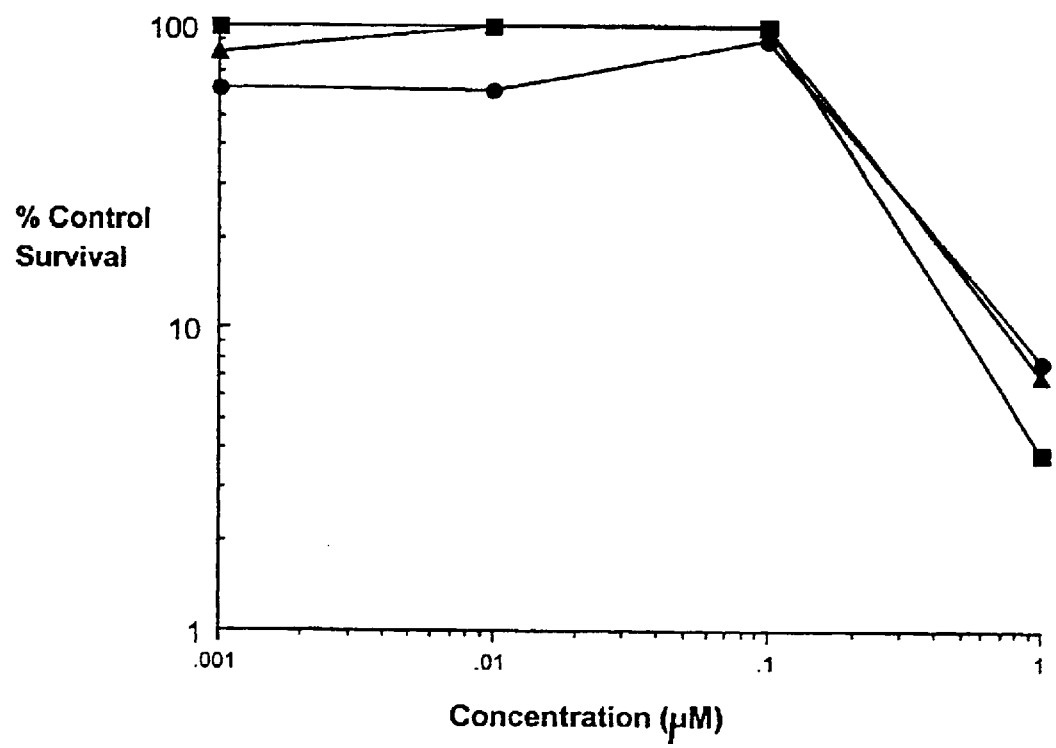
FIG. 8 is a graph illustrating the cytotoxicity of the compound made by the scheme shown in FIG. 2.

The cytotoxicity of the PBD released from resin 12 following irradiation was determined using the MTT assay. The survival curve resulting from the compound released from 12 (JMB 98) following 2 and 5 hours irradiation was consistent with that of authentic 13 (AG 105); see FIG. 8. The released PBD therefore has full biological activity.

EXAMPLE 7

Figure 9:
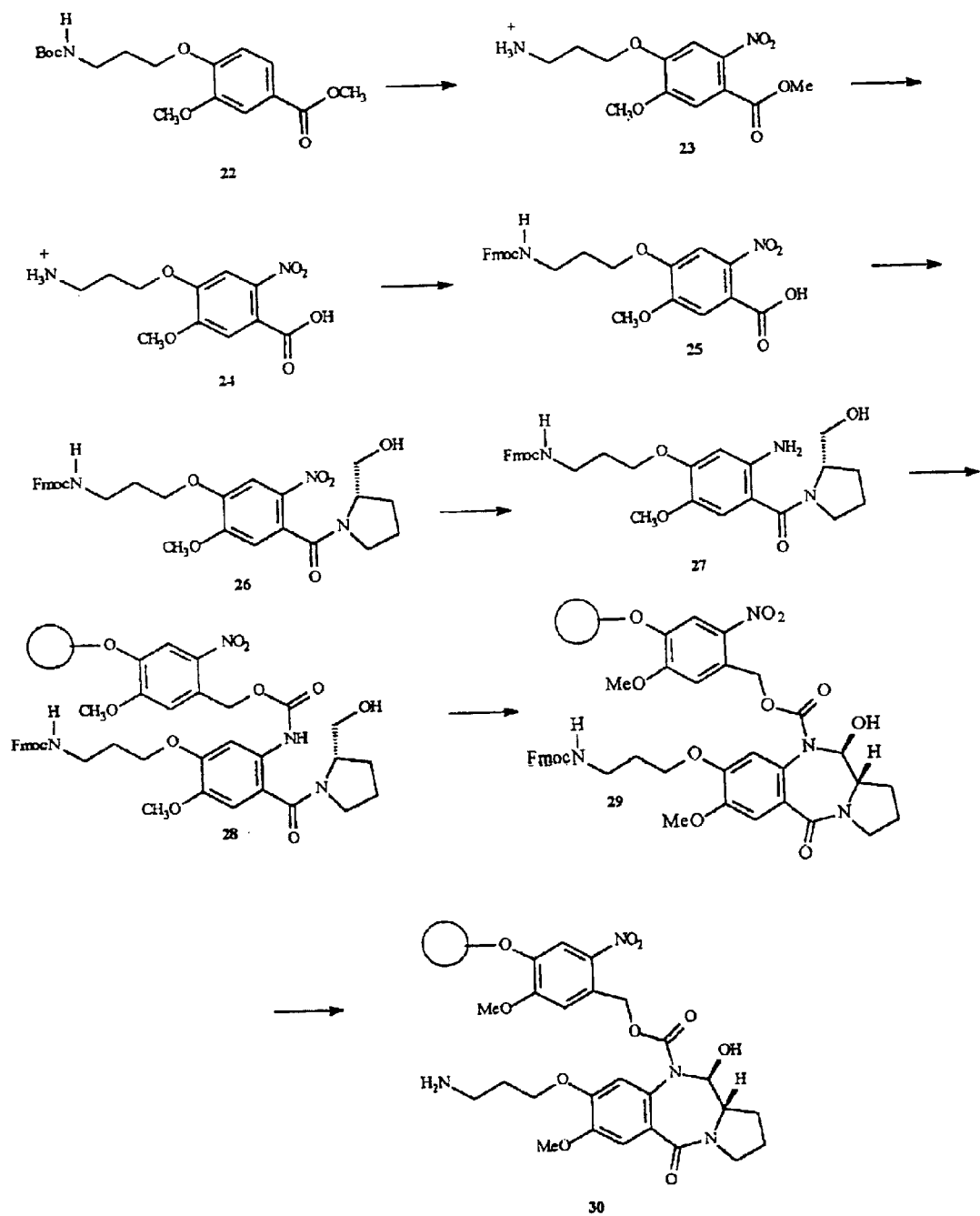
FIGS. 9–12 are a synthesis scheme for further compounds according to the invention.

Synthesis of a Resin-bound 8-aminopropyl PBD Scaffold (30)(see FIG. 9)

Overall Synthetic Strategy

The o-nitrobenzylchloroformate resin 2 can also immobilize more complicated amines other than simple anthranilic acids, greatly facilitating the preparation of molecules such as the PBD C8-amino scaffold 30. As in the previous strategy, the Fmoc protected scaffold 29 was prepared by oxidizing the primary alcohol resin 28. This resin was obtained by loading the o-nitrobenzylchloroformate resin 2 with the amino alcohol 27. The amino alcohol was prepared by a Tin (II) chloride mediated reduction of the nitro alcohol 26; use of hydrogenation conditions to reduce the nitro group were avoided due to the presence of the Fmoc group in 26. The nitro alcohol in turn was furnished in this case by coupling pyrrolidine methanol 5 to the o-nitrobenzoic acid 25, although other functionalised prolines could also be employed in the coupling reaction. The Fmoc o-nitrobenzoic acid was obtained via Fmoc protection of the amino acid 24 produced by hydrolysis of the ester 23. Other nitrogen protecting groups may be substituted for Fmoc as long as the cleavage conditions involved are compatible with the presence of an o-nitrobenzyl carbamate linker (eg. Boc, Alloc, Teoc etc). Finally, the amino ester was prepared by nitration of 22 which was obtained by a Mitsunobu etherification of commercially available methyl vanillate.

Boc Amino Ester (22)

A solution diethylazidodicarboxylate (3.38 g, 19.4 mmol) in THF (50 mL) was added dropwise to a solution of methylvanillate (3.53 g, 19.4 mmol), N-Boc-propanolamine (3.4 g, 19.4 mmol) and triphenylphosphine (5.09 g, 19.4 mmol) in THF (50 mL) at 0° C. The reaction mixture was allowed to warm to room temperature and stir overnight. Excess solvent was removed by rotary evaporation under reduced pressure and the residue triturated with toluene. Precipitated triphenylphosphine oxide was removed by vacuum filtration and the filtrate concentrated in vacuo. The residue was subjected to flash column chromatography (silica gel, petroleum ether 40–60/ethyl acetate, 80/20) and removal of excess eluent afforded the pure product 22 (4.8 g, 73% yield.). $^1$H NMR (270 MHz, $CDCl_3$) δ 7.65 (dd, J=8.43, 2.02 Hz, 1H), 7.54 (d, J=2.02 Hz, 1H), 6.86 (d, J=8.43 Hz, 1H), 5.55 (bs, 1H), 4.15 (t, J=5.87 Hz, 2H), 3.93 (s, 3H), 3.90 (s, 3H), 3.41–3.35 (m, 2H), 2.09–2.00 (m, 2H) and 1.46 (s, 9H). $^{13}$C NMR (68.7 MHz, $CDCl_3$) δ 166.9, 156.1, 152.1, 148.8, 123.5, 122.8, 112.0, 111.2, 79.0, 68.2, 55.9, 52.0, 38.9, 29.2 and 28.5.

Amino Nitro Ester (23)

The Boc-protected amine 22 (10 g) was added portionwise to cold nitric acid (30 mL, 70%, ice bath), the reaction mixture was allowed warm to room temperature and stir overnight. The reaction mixture was poured onto crushed ice (100 g) and the resulting aqueous solution reduced to half its original volume by rotary evaporation under reduced pressure. The resulting precipitate was collected by vacuum filtration and recrystallised from absolute ethanol to afford the product as a yellow crystalline solid 23 (8.9 g, 87%). $^1$H NMR (270 MHz, CDCl$_3$) δ 7.47 (s, 1H), 7.08 (s, 1H), 4.24 (t, J=5.86 Hz, 2H), 3.96, (s, 3H), 3.89 (s, 3H), 3.24 (t, J=6.78, 2H) and 2.32–2.23 (m, 2H).

Amino Nitro Acid (24)

A solution of potassium hydroxide (0.5 g, 8.7 mmol) and the nitrobenzoic acid 23 (1 g, 2.9 mmol) in aqueous methanol (H$_2$O, 10 mL; methanol, 20 mL) was allowed to stir at room temperature for 1 hour and then heated at reflux until TLC (AcOEt, MeOH, TEA, 1:10:100) revealed the complete consumption of starting material. Excess methanol was removed by rotary evaporation and the residual solution diluted with water and neutralised with 1N HCl. The neutralised aqueous solution was used directly, without further purification, in the next synthetic step.

Fmoc Nitro Acid (25)

Fluorenylmethyl chloroformate (0.78 g, 3 mmol) was added portionwise to the aqueous solution from the previous reaction which had been diluted with THF (50 mL) and aqueous sodium carbonate (2.15 g, 50 mL water). The reaction mixture was then allowed to stir overnight. Excess organic solvent was removed by rotary evaporation under reduced pressure from the reaction mixture, the residual aqueous solution was then washed with ethyl acetate (3×20 mL) (to remove excess Fmoc-Cl). The aqueous phase was acidified with conc. HCl and extracted with ethyl acetate (2×50 mL). The organic phase was dried over magnesium sulphate, filtered and evaporated in vacuo to afford the product 25 (1 g, 70% yield). $^1$H NMR (270 MHz, CDCl$_3$) δ (Rotamers) 8.21 (bs, 2H), 7.73 (d, J=7.14 Hz, 2H), 7.59 (d, J=7.33 Hz, 2H) 7.40–7.13 (m, 5H), 6.47 and 5.70 (2×bs, 1H), 4.54–3.88 (m, 5H), 3.77 (s, 3H), 3.44–3.42 (m, 2H) and 2.04–1.90 (m, 2H). $^{13}$C NMR (68.7 MHz, CDCl$_3$) δ 168.7, 156.9, 152.1, 149.8, 143.7, 141.9, 141.3, 127.7, 127.0, 124.9, 120.6, 120.0, 111.1, 107.8, 68.5, 66.4, 56.4, 47.3, 39.1 and 28.4.

Fmoc Nitro Alcohol (26)

A catalytic amount of DMF (2 drops) was added to a solution of the acid 25 (1.16 g, 2.36 mmol) and oxalyl chloride (0.33 g, 2.6 mmol) in dry dichloromethane (20 mL) and the reaction mixture was allowed to stir overnight. The resulting acid chloride solution was cooled to 0° C. and treated dropwise with a solution o,f pyrrolidinemethanol (0.26 g, 2.57 mmol) and triethylamine (0.52 g, 5.14 mmol) in dry dichloromethane (15 mL). Thin layer chromatography, performed shortly after the end of the addition of amine, revealed that reaction had gone to completion. The reaction mixture was washed with HCl (1N, 1×50 mL) and water (2×20 mL) and dried over magnesium sulphate. Removal of excess solvent afforded the crude product which was subjected to flash column chromatography (silica gel, gradient elution, 1% methanol in chloroform to 2% methanol in chloroform) to afford the required amide 26 (1.1 g, 81%). $^1$H NMR (270 MHz, CDCl$_3$) δ 7.75 (d, J=7.33 Hz, 2H), 7.67 (s, 1H), 7.60 (d, J=6.96 Hz, 2H), 7.41–7.26 (m, 4H), 6.78 (s, 1H), 5.66 (bs, 1H), 4.48–4.39 (m, 3H), 4.23–4.13 (m, 3H), 3.91–3.79 (m, 5H), 3.45–3.42 (m, 2H), 3.18–3.13 (m, 2H) and 2.08–1.70 (m, 6H). $^{13}$IC NMR (68.7 MHz, CDCl$_3$) δ 168.5, 156.5, 154.7, 148.2, 143.9, 141.3, 137.0, 128.0, 127.7, 127.0, 124.9, 120, 108.9, 108.0, 68.4, 66.2, 66.0, 61.5, 56.6, 53.5, 47.3, 39.0, 28.9, 28.4 and 24.4.

Fmoc Amino Alcohol (27)

A solution of the nitroamide 26 (3 g, 5.22 mmol) and SnCl$_2$ 2H$_2$O (6.15 g, 27.15 mmol) in methanol (60 mL) was heated at reflux for 2 hours. The reaction mixture was concentrated to ⅓ of its original volume and carefully treated with saturated aqueous sodium bicarbonate solution (vigorous effervescence!) until pH8 was obtained. The mixture was allowed to stir vigorously with ethyl acetate (100 mL) overnight and then filtered through celite to remove precipitated tin salts. The aqueous phase was extracted with ethyl acetate (50 mL) and the combined organic phase was dried over magnesium sulphate. Removal of excess solvent afforded the desired amine as a dark yellow oil 27 (1.93 g, 68%). $^1$H NMR (270 MHz, CDCl$_3$) δ 7.75 (d, J=7.51 Hz, 2H), 7.61 (d, J=7.33 Hz, 2H), 7.40–7.26 (m, 4H), 6.72 (s, 1H), 6.25 (s, 1H), 5.95 (bs, 1H), 4.43–4.04 (m, 6H), 3.67–3.42 (m, 9H) and 2.11–1.7 (m, 6H). $^{13}$C NMR (68.7 MHz, CDCl$_3$) δ 171.7, 156.6, 150.8, 144.0, 141.3, 140.6, 127.6, 127.0, 125.0, 119.9, 112.0, 102.2, 68.0, 66.6, 66.4, 61.0, 56.6, 51.0, 47.3, 39.5, 29.1, 28.5 and 24.9.

Resin-bound Amino-alcohol (28)

The o-nitrobenzylchloroformate resin (0.048 mmol) was allowed to swell for 10 minutes in dry dichloromethane (5 mL). A solution of the amino alcohol (0.13 mg, 0.24 mmol) and pyridine (0.02 g) in dry dichloromethane (1 mL) was added to the resin suspension under a nitrogen atmosphere at 0° C. The reaction mixture was then allowed to shake overnight at room temperature. Excess reagent was removed by suction and the resin washed with dichloroinethane (2×5 mL) and methanol (2×5 mL) and then dried in vacua overnight. The procedure was repeated three times to ensure complete reaction.

Resin-bound Fmoc-aminopropyl PBD (29)

The carbamate resin (0.048 mmol) prepared in the previous reaction was allowed to swell in dry dichloromethane (1 mL) for 10 minutes. The suspension was cooled to −10° C. and treated successively with triethylamine (20 μL, 0.144 mmol) and pyridine sulphur trioxide complex (0.023 g, 0.144 mmol) in dimethyl sulphoxide (0.5 mL) at −10° C. and the suspension was allowed to shake at −10° C. for two hours. Excess reagent was removed by suction and the resin washed with methanol (2×5 mL) and dichloromethane (2×5 mL) and then dried in vacuo overnight. The procedure was repeated three times to ensure complete reaction.

Resin-bound Aminoporopyl PBD (30)

The resin-bound 8-aminopropyl PBD 30 is prepared from the Fmoc-protected form 29 by standard deprotection conditions. This compound 30 can be used to form compounds according to the second aspect of the present invention, by reaction of appropriate combinatorial units from those described above with this compound.

EXAMPLE 8

Figure 10:
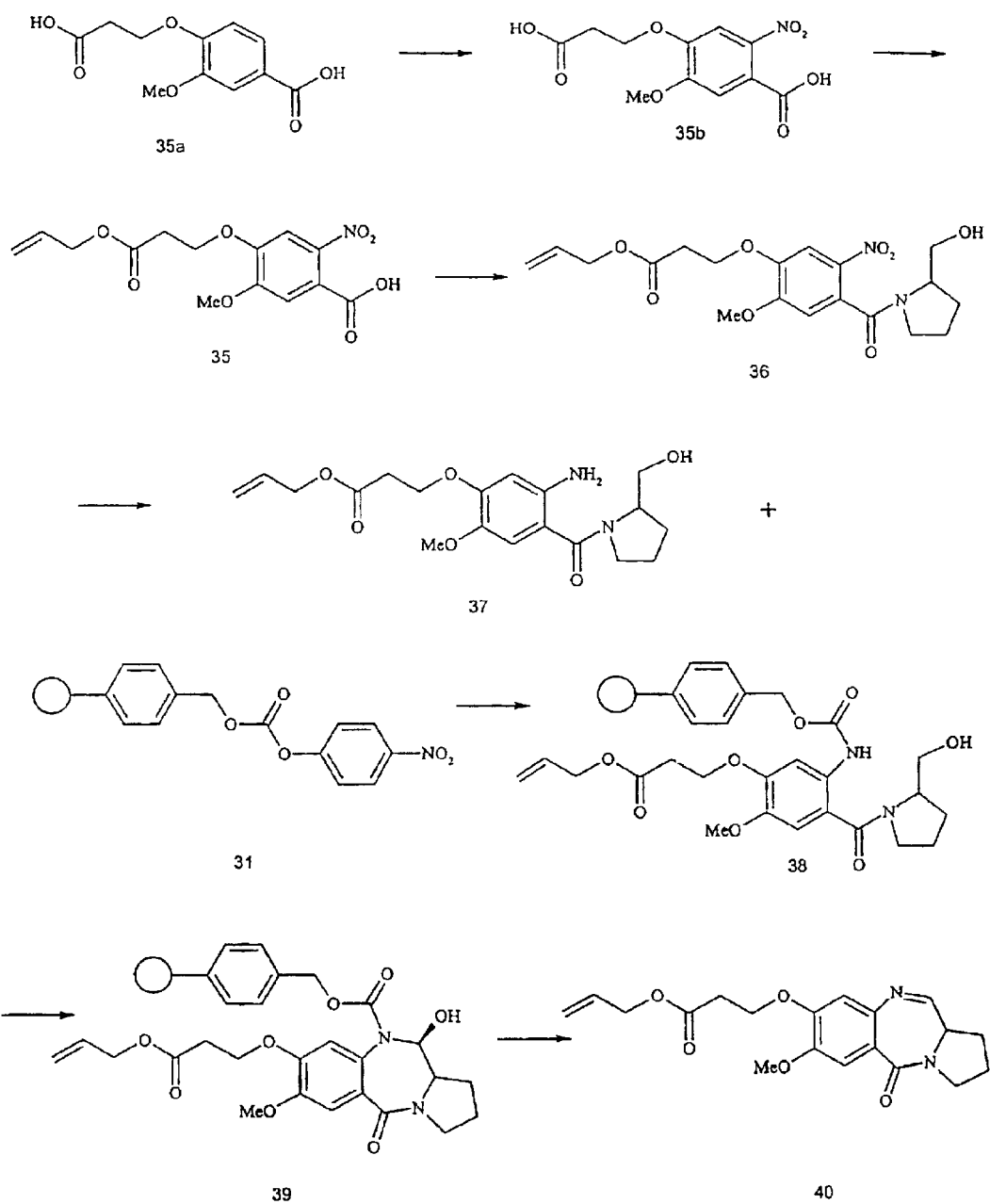

Synthesis of Resin Bound 8-allyl Ester Protected Acid PBD Scaffold (39) (see FIG. 10)

The resin bound PBD 39 was synthesised following the strategy used in Example 4.

Synthesis of Amine 37

The nitro acid 35 was derived from the alcohol 35a by the following two steps.

The alcohol 35a (50 g, 0.22 mol) was added portionwise over 1 hour to nitric acid (70%, 400 ml) cooled to 0° C. Once addition was complete, the solution was stirred at 0° C. for 1 hour, then allowed to warm to room temperature. The semisolid formed was collectedby filtration and washed with a minimum of ice/water. The resulting pale yellow solid was redissolved in EtOAc, the solution dried (MgSO$_4$) and then concentrated to afford the diacid 35b (31 g, 49%).

$^1$H NMR (270 MHZ): δ 2.83–2.79 (t, J=6, 12.5 HZ, 2H), 3.94 (s, 3H), 4.37–4.33 (t, J=6, 12.5 HZ, 2H), 7.18 (s, 1H), 7.46 (s, 1H), 10.38 (br. s, 2H).

A mixture of the diacid 35b (20 g, 74.3 mmol) and p-toluene sulphonic acid monohydrate (2.3 g, 7.4 mmol) in allyl alcohol (240 mL, 3.5 mol) was refluxed for 7 hours then allowed to cool. The allyl alcohol was then removed in vacuo, and the residue triturated with dilute HCl acid (3×75 ml) and collected by filtration. This solid was taken up in EtOAc, and the resulting solution washed with water (3×50 ml) and brine (3×50 ml) and dried over sodium sulphate. Evaporation in vacuo afforded 35 as a white solid (19.27 g, 84%): mp 128–130° C.;

$^1$H-NMR (270 MHZ, CDCl$_3$) δ 2.92 (t, 2H, J=6.35 Hz); 3.94 (s, 3H); 4.38 (t, 2H, J=6.41 Hz); 4.65 (d, 2H, J=5.61 Hz); 5.27 (dd, 1H, J$_1$=1.28 Hz, J$_2$=19.42 Hz); 5.33 (dd, 1H, J$_1$=1.28 Hz, J$_2$=17.04 Hz); 5.92 (m, 1H); 7.15 (s, 1H); 7.45 (s, 1H); $^{13}$C NMR (67.8 MHZ, CDCl$_3$): δ 34.1, 56.5, 65.0, 65.4, 108.5, 111.3, 118.3, 122.9, 131.8, 141.1, 149.1, 152.6, 167.1, 170.0; IR (Nujol); v 1730, 1630, 1550, 1430, 1390, 1290, 1230, 1190, 1170, 1070, 1030, 1010 cm$^{31\ 1}$; MS (EI) m/z (relative intensity): 325 (M$^+$, 19), 251 (3), 213 (2), 196 (3), 211 (3), 113 (19), 91 (4), 71 (9), 55 (6); HRMS: calcd. for C$_{14}$H$_{15}$NO$_8$ 325.0798, found 232.0773.

To a suspension of the nitro acid 35 (5 g, 0.015 mol) in CH$_2$Cl$_2$ (75 ml) was added oxalyl chloride (1.5 ml, 0.017 mol) and DMF (0.05 ml) in a dropwise manner and the resulting solution was stirred for 16 hours. The acid chloride was then added dropwise to a stirring solution of pyrrolidine methanol (1.7 g, 0.017 mol) and triethylamine (4.7 ml, 0.034 mol) in CH$_2$Cl$_2$ (40 ml) at −20° C. (liquid N$_2$/acetone). This solution was stirred at room temperature for 16 hours. The reaction was quenched with aqueous HCl (1.0 N, 25 ml) and the organic extracts were washed with H$_2$O and brine, dried and concentrated to give the crude yellow oil. The material was purified by column chromatography (5% MeOH/CHCl$_3$), to give 36 as a pale yellow oil (6.2 g, 100%). $^1$HNMR (270 MHz, CDCl$_3$) δ 2.22–1.71 (m, 6H); 2.94 (t, J=6.4 Hz, 2H); 3.15 (dxd, J=6.5 Hz, 2H); 3.92–3.76 (m, 1H); 3.96 (s, 3H); 4.4 (t, J=6.2 Hz, 2H); 4.67–4.64 (m, 2H); 5.39–5.23 (m, 2H); 6.0–5.86 (m, 1H); 6.81 (s, 1H); 7.75 (s, 1H).

To a stirring solution of the nitro compound 36 (6 g, 0.015 mol) in MeOH (80 ml) was added SnCl$_2$.2H$_2$O (16.6 g, 0.074 mol) and heated at reflux for 45 minutes. The reaction was concentrated in vacuo and the residual oil was partitioned between EtOAc and aqueous saturated NaHCO$_3$ and stirred vigorously for 16 hours to aid separation. This material was filtered through Celite and extracted with EtOAc, washed with H$_2$O and brine, dried and concentrated to give amine 37 as a yellow oil (3.3 g, 59%). $^1$H NMR (270 MHz, CDCl$_3$) δ 2.17–1.65 (m, 6H); 2.9 (t, J=6.6 Hz, 2H); 3.72–3.46 (m, 3H); 3.75 (s, 3H); 4.2 (t, J=6.8 Hz, 2H); 4.4 (br. dxd, J=9.7 Hz, 2H); 4.65–4.62 (m, 2H); 5.37–5.22 (m, 2H); 6.0–5.85 (m, 1H); 6.3 (s, 1H); 6.76 (s, 1H).

Synthesis of PBD Scaffold 39

A suspension of p-nitrophenyl carbamate Wang resin 31 (1 g, 0.6 mmol/g loading) in CH$_2$Cl$_2$/DMF (2:1, 15 ml) was shaken for 30 minutes. A solution of amine 37 (1.13 g, 3 mmol), HOBt (0.24 g, 1.8 mmol) and DIPEA (0.63 ml, 3.6 mmol) in CH$_2$Cl$_2$/DMF (2:1, 15 ml) was added to the swollen resin. The vessel was allowed to shake at room temperature for 6 hours. Resin 38 was filtered and rinsed with DMF (2×10 ml), CH$_2$Cl$_2$ (2×10 ml), MeOH (2×10 ml), Et$_2$O (10 ml) and dried in vacuo.

A suspension of resin 38 (0.6 mmol) in CH$_2$Cl$_2$ (10 ml) was allowed to shake for 30 min. A solution of Dess Martin periodinane (1.27 g, 3 mmol) in CH$_2$Cl$_2$ (20 ml) was added to the swollen resin. The vessel was allowed to shake at room temperature for 2 hours. Resin 39 was filtered and rinsed with CH$_2$Cl$_2$ (2×10 ml), MeOH (2×10 ml), Et$_2$O (10 ml) and dried in vacuo.

This scaffold 39 could be used in combinatorial chemistry by deprotection of the acid group using Pd(PPh$_3$)$_4$ in chloroform, acetic acid and n-methyl morpholine.

A suspension of resin 39 (0.6 mmol) in TFA/CH$_2$Cl$_2$ (1:1, 30 ml) was allowed to shake for 2 hours. The resultant red solution was decanted off and was diluted with water (20 ml) and carefully neutralised to pH 7.0 by the addition of solid sodium bicarbonate. The organic phase was separated and washed with H$_2$O (3×20 ml), brine (2×20 ml), dried (MgSO$_4$) and concentrated to give a brown foam 40 (0.09 g, 42%). EIMS 358 (M+1)$^+$.

EXAMPLE 9

Figure 11:
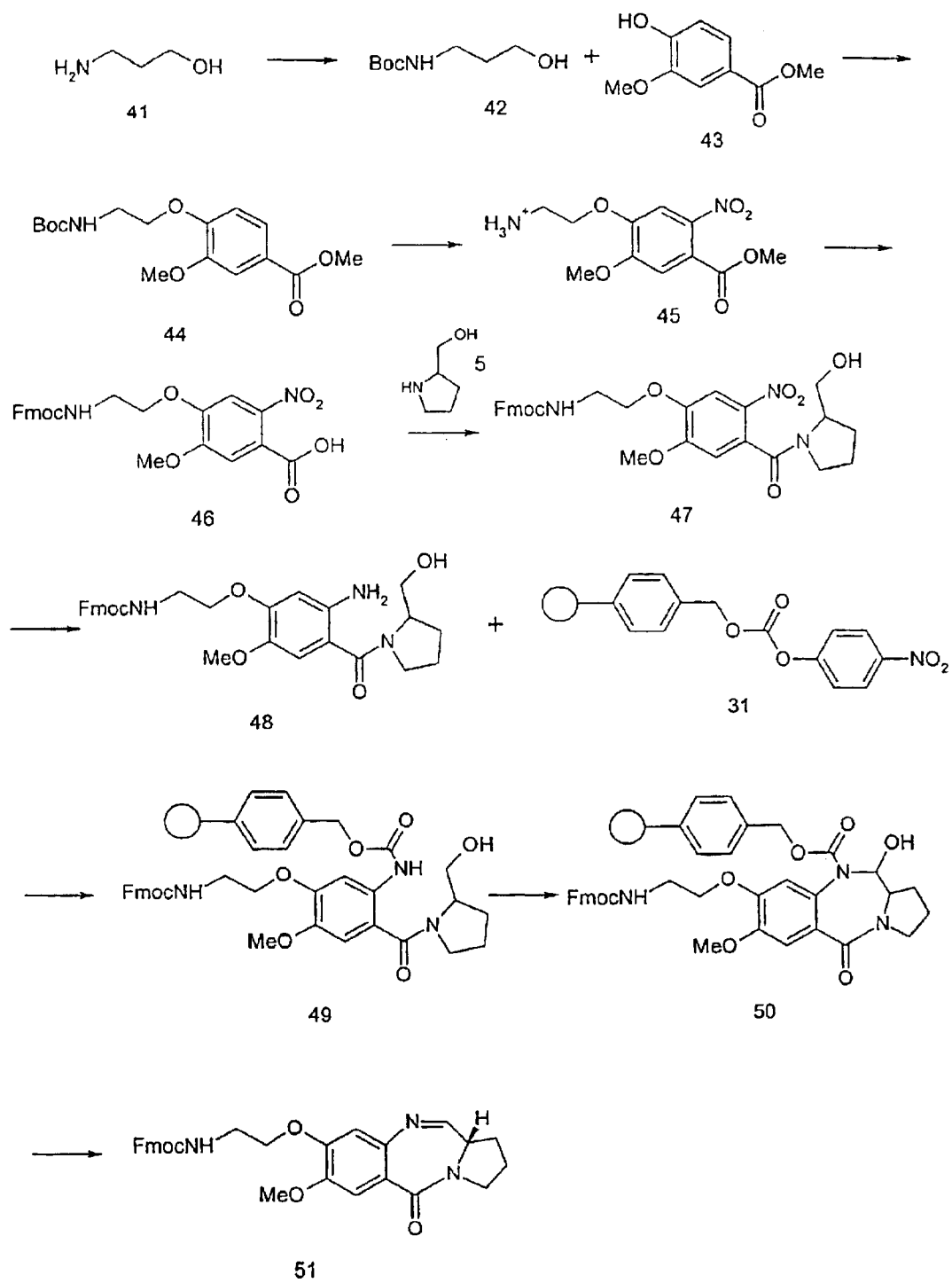

Synthesis of an Aminopropyloxy PBD Scaffold (50) (See FIG. 11)

Overall Synthesis Strategy

The on-bead (p-nitrophenyl Wang resin) ring closure (49–50) was carried out using a Dess Martin reagent as in Example 4. The final step (production of the off-bead PBD), was carried out to prove that the on-bead resin was of the desired structure.

Synthesis of N-(tert-butoxycarbonyl)-3-hydroxypropylamine 42

A solution of (Boc)$_2$O (25.0 g, 114.5 mmol) in anhydrous DCM (50 mL) was added dropwise to a stirred solution of 3-amino-1-propanol 41 (7.8 g, 104.5 mmol) in anhydrous DCM (100 mL), under a nitrogen atmosphere. The reaction mixture was allowed to stir for 12 hours, after which time TLC (50% pet-ether/EtOAc) revealed complete loss of starting material. The solution was diluted with Et$_2$O (150 mL) and washed with phosphate buffer (0.5 M, pH 5.4, 2×70 mL), sat. aqueous NaHCO$_3$ (70 mL), brine (2×70 mL) and dried over MgSO$_4$. Excess solvent was removed by evaporation under reduced pressure to give a viscous colourless oil (18.3 9, 100%).

$^1$H NMR (270 MHz, CDCl$_3$): δ 1.44 (s, 9H, CH$_3$), 1.67 (m, 2H, H2'), 3.26 (q, 2H, J=6.23 Hz, H3'), 3.65 (dd, 2H, J=5.86, 5.68 Hz, H1'), 3.78 (dt, 1H, J=6.04, 5.87 Hz, OH), 5.18 (br, 1H, NH); $^{13}$C NMR (67.8 MHz, CDCl$_3$): δ 28.4 (CH$_3$), 32.6 (C2'), 37.1 (C3'), 59.3 (C1'), 79.4 (C$_{quater}$), 157.1 (C=O); MS (E/I) m/z (relative intensity): 176 (M$^+$, 30), 120 (100), 119 (31), 102 (49), 83 (33), 76 (67), 74 (36); HRMS (E/I) exact mass calcd for C$_8$H$_{17}$O$_3$N: m/e 175.1200, obsd m/e 175.1208; IR (Nujol) v: (cm$^{-1}$) 3355, 2976, 2936, 2878, 1810, 1694, 1531, 1455, 1392, 1366, 1278, 1253, 1173, 1072, 996, 914, 870, 781, 752, 638.

Synthesis of Methyl 4-[N-(tert-butoxycarbonyl)] aminotropyloxy-3-methoxybenzoate 44

A solution of DEAD (18.3 g, 105.3 mmol) in freshly distilled THF (50 ml) was added dropwise to a mechanically stirred solution of triphenylphosphine (27.6 g, 105.3 mmol), methyl vanillate 43 (19.2 g, 105.3 mmol), and Boc-amino-1-propanol 42 (18.4 g, 105.3 mmol) in freshly distilled THF (250 mL), at 0° C. under a nitrogen atmosphere. Following the addition of DEAD the reaction mixture was allowed to stir at room temperature overnight and the progress of reaction was monitored by TLC (50% EtOAc/pet-ether). The solvent was removed by evaporation under reduced pressure and the residue was triturated with $Et_2O$ (300 mL). This led to the precipitation of some of the TPO and diethyl hydrazinedicarboxylate which were removed by filtration and the filtrate was washed with 1 N aqueous NaOH (150 mL), $H_2O$ (2×150 mL), brine (2×150 mL) and dried over $MgSO_4$. Excess solvent was removed by evaporation under reduced pressure. The title compound was purified by column chromatography (80% pet-ether/EtOAc) to give a beige solid (30 g, 85%).

mp=79–82° C.; $^1$H-NMR ($CDCl_3$, 270 MHz): δ 1.46 (s, 9H, $CH_3$), 2.0–2.08 (m, 2H, H2'), 3.38 (dd, 2H, J=5.68, 6.04 Hz H3'), 3.90 (s, 3H, $OCH_{3ether}$), 3.93 (s, 3H, $OCH_{3ethex}$), 4.14 (t, 2H, J=5.95 Hz, H3'), 5.58 (br, 1H, NH), 6.86 (d, 1H, J=8.42 Hz, H5), 7.55 (d, 1H, J=1.83 Hz, H2), 7.65 (dd, 1H, J=2.02, 8.42 Hz, H6); $^{13}$C-NMR ($CDCl_3$, 68.7 MHz): δ 28.5 (C), 29.2 (C2'), 38.9 (C3'), 52.0 ($OCH_{3aster}$), 55.8 ($OCH_{3ether}$), 68.1 (C1'), 78.9 ($C_{quater}$), 111.3 (C5), 112.0 (C2), 122.84 ($C_{arom}$), 123.5 (C6), 148.8 ($C_{arom}$), 152.1 ($C_{arom}$), 156.1 (NC=O), 166.8 (C=O); MS (E/I) m/z (relative intensity): 339 (M$^+$, 11), 266 (13), 182 (42), 151 (27), 102 (100); HRMS (E/I) exact mass calcd. for $C_{17}H_{25}NO_6$: m/e 339.1682, obsd m/e 339.1733; IR (Nujol) v: (cm$^{-1}$) 3362, 2923, 2854, 1712, 1684, 1599, 1520, 1464, 1377, 1272, 1217, 1132, 1045, 1022, 872, 780, 762, 722.

Synthesis of Methyl 4-Aminoproryloxy-5-methoxy-2-nitrobenzoate 45

The ester 44 (4.0 g, 11.8 mmol) was added in small portions to a stirred solution of 70% $HNO_3$ (2 mL acid/g of substrate) at room temperature and the reaction mixture was allowed to stir overnight. TLC ($CHC_3$) at this point revealed the complete loss of starting material. The reaction mixture was cooled on ice bath, and 15 g of iced water was added, precipitating the product. The precipitate was collected by vacuum filtration and washed with small amount of iced water. The filtrate was cooled and a second crop of precipitate was collected by vacuum filtration and washed with iced water. The combined precipitate was dried in vacuo to provide the title compound 45 as a yellow solid, which was not purified further, but used directly in the subsequent reaction (2.3 g, 70%).

mp=101–103° C.; $^1$H-NMR ($CDCl_3$/DMSO-$d_6$, 270 MHz): δ 2.31 (m, 2H, H2'), 3.20 (br, 2H, H3'), 3.95 (s, 3H, $OCH_{3ether}$), 3.98 (s, 3H, $OCK_{3ester}$), 4.24 (t, 2H, J=5.95 Hz, H1'), 7.11 (s, 1H, H6), 7.49 (s, 1H, H3), 8.21 (s, 3H, NH); $^{13}$C-NMR ($CDCl_3$, 68.7 MHz): δ 26.5 (C2'), 37.0 (C3'), 53.0 ($OCH_{3ester}$), 56.0 ($OCH_{3ether}$), 66.7 (C1'), 108.3 (C3), 111.0 (C6), 121.6 ($C_{arom}$), 140.9 (C2), 149.3 ($C_{arom}$), 152.6 ($C_{arom}$), 166.8 (C=O); MS (E/I) m/z (relative intensity): 284 (M$^+$, 90), 237 (70), 227 (93), 196 (47), 181 (38), 137 (100), 122 (81), 93 (52), 79 (44); ERMS (E/I) exact mass calcd. for $C_{12}H_{17}N_2O_6$: m/e 284.1008, obsd m/e 284.1018; IR (Nujol) v: (cm$^{-1}$) 3472, 2937, 2911, 2855, 1733, 1532, 1516, 1462, 1377, 1292, 1224, 1143, 1052, 884, 812, 792, 773, 756, 724, 646.

Synthesis of Methyl 4-(N-9-fluorenylmethoxycarbonyl) aminopropyloxy-5-methoxy-2-nitrobenzoic Acid 46

A solution of 45 (3.9 g, 11.2 mmol) and KOH (1.9 g, 33.4 mmol) in aqueous methanol (77 mL MeOH, 15 mL $H_2O$) was heated at reflux for 90 minutes. At which time TLC (EtOAc/MeOH/TEA 100:10:1) revealed complete consumption of starting material. Excess MeOH was removed by evaporation under reduced pressure and the concentrate diluted with $H_2O$ (20 mL). The aqueous solution was neutralised with conc. HCl, diluted with THP (100 mL) and sodium carbonate (2.9 g, 27.9 mmol) was added to adjust the solution to pH 9. After this, fluorenylmethyl chloroformate (3.0 g, 11.6 mmol) was added portionwise over 30 minutes and the reaction mixture was allowed to stir for 12 hours. Excess THP was removed by evaporation under reduced pressure and the aqueous fraction was extracted with EtOAc (3×100 mL) to remove free Fmoc, and then acidified with conc. HCl and extracted again with EtOAc (3×100 mL). The organic phase was washed with $H_2O$ (2×100 mL), brine (100 mL), dried over $MgSO_4$ and excess solvent was removed by evaporation under reduced pressure to afford 46 as a beige solid which was not purified further, but used directly in the subsequent reaction (4.7 g, 86%).

mp=145–146° C.; $^1$H-NMR ($CDCl_3$, 270 MHz): δ 1.81 (m, 2H, H2'), 3.43 (m, 2H, H3'), 3.78 (s, 3H, $OCH_3$), 4.08–4.23 (m, 3H, H1'+Fmoc CH), 4.49 (d, 2H, J=6.41 Hz, Fmoc $CH_2$), 5.70 (br, 1H, NH), 7.14 (s, 1H, H6), 7.26–7.41 (m, 5H, Fmoc$_{aryl}$+H3), 7.59 (d, 2H, J=7.51 Hz, Fmoc$_{aryl}$), 7.74 (d, 2H, J=7.15 Hz, Fmoc$_{aryl}$), 9.62 (s, 1H, $CO_2H$); $^{13}$C-NMR ($CDCl_3$, 68.7 MHz): δ 28.8 (C2'), 39.1 (C3'), 47.2 (CH Fmoc), 56.4 ($OCH_3$), 66.3 ($CH_2$ Fmoc), 68.5 (C1'), 107.9 (C3), 111.1 (C6), 120.0, 124.9, 127.1 and 127.7 (CH Fmoc$_{aryl}$), 128.0 ($C_{arom}$), 137.0 ($C_{arom}$), 141.3 (C Fmoc$_{aryl}$), 143.8 (C Fmoc$_{aryl}$), 148.2 ($C_{arom}$), 154.7 ($C_{arom}$), 156.8 (NC=O) 171.5 ($CD_2H$); MS (FAB) m/z (relative intensity): 493 (M$^+$+1, 3), 297 (6), 271 (4), 191 (18), 180 (21), 179 (100), 178 (67), 165 (30), 102 (17), 93 (13); HRMS (FAB) exact mass calcd. for $C_{26}H_{25}N_2O_8$ (M+H): m/e 493.1532, obsd m/e 493.1536; IR (Nujol™) v: (cm$^{-1}$) 1712, 1535, 1463, 1377, 1277, 1219, 1081, 970, 762, 722, 656.

Synthesis of (2S)-N-[4-(N-9-fluorenylmethoxycarbonyl)aminotropyloxy-5-methoxy-2-nitrobenzoyl)]pyrrolidine-2-methanol 47

A catalytic amount of DMF (2 drops) was added to a solution of the nitrobenzoic acid 46 (8.0 g, 16.3 mmol) and oxalyl chloride (2.3 g, 17.9 mmol) in anhydrous DCM (120 mL), at room temperature under a nitrogen atmosphere. The reaction mixture was stirred for 16 hours and the resulting solution of acid chloride was cooled to 0° C. (ice/acetone) under a nitrogen atmosphere. A solution of pyrrolidinemethanol (1.8 g, 17.9 mmol) and DIPEA (4.6 g, 35.77 mmol) in anhydrous DCM (40 mL) was added dropwise over 30 minutes. Once the addition was complete, the reaction mixture was allowed to warm to room temperature. Stirring was continued for a further 2 hours, at which time TLC (95% EtOAc/MeOH) revealed complete reaction. The reaction mixture was washed with 1 N aqueous HCl (2×100 mL), $H_2O$ (2×100 mL), brine (100 mL), and dried over $MgSO_4$. Excess solvent was removed by evaporation under reduced pressure to give the crude compound as a brown oil. Purification by flash column chromatography (99% $CHCl_3$/MeOH) afforded the pure amide 47 as a beige solid (5.6 g, 82%)

[α]$_D$–53.3° (c=1.03, $CHCl_3$); mp=78–81° C.; $^1$H-NMR ($CDCl_3$, 270 MHz): δ 1.69–1.88 (m, 4H, H4+H3), 2.04–2.12 (m, 2H, H2'), 3.16 (m, 2H, H3'), 3.45 (m, 2H, H5), 3.81 (s, 3H, $OCH_3$), 3.86–3.91 (m, 2H, $CH_2$—OH), 4.08–4.24 (m, 3H, H1'+Fmoc CH), 4.38–4.48 (m, 3H, H2+Fmoc $CH_2$), 5.65 (br, 1H, NH), 6.78 (s, 1H, H6$_{arom}$), 7.27–7.42 (m, 5H, H3 $_{arom}$+Fmoc$_{aryl}$), 7.61 (d, 2H, J=7.32 Hz, Fmoc$_{aryl}$), 7.76

(d, 2H, J=7.32 Hz, Fmoc$_{aryl}$); $^{13}$C-NMR (CDCl$_3$, 68.7 MHz): δ 24.4 (C4), 28.4 (C3), 28,9 (C2'), 39.1 (C3'), 47.3 (CH Fmoc), 49.5 (C5), 56.6 (OCH$_3$), 60.4 (C2), 61.5 (CH$_2$—OH), 66.2 (CH$_2$ Fmoc), 68.5 (C1'), 108.0 (C3$_{arom}$), 108.9 (C6$_{arom}$), 120.0, 124.9, 127.0 and 127.7 (CH Fmoc$_{aryl}$), 128.0 (C$_{arom}$), 137.0 (C$_{arom}$), 141.3 (C Fmoc$_{aryl}$), 143.9 (C Fmoc$_{aryl}$), 148.2 (C$_{arom}$), 154.7 (C$_{arom}$), 156.5 (NC=O$_{carbamate}$), 171.2 (C=O$_{emide}$); MS (FAB) m/z (relative intensity): 576 (M$^+$1, 32), 191 (18), 179 (100). 165 (25), 102 (33); HRMS (FAB) exact mass calcd for C$_{312}$H$_{34}$N$_3$O$_8$ (M+H): m/e 576.2268 obsd m/e 576.225; IR (Nujol) v: (cm$^{-1}$) 2626, 1714, 1615, 1576, 1520, 1452, 1434, 1333, 1276, 1218, 1147, 1059, 869, 818, 759, 742.

Synthesis of (2S)-N-[4-(N-9-fluorenylmethoxycarbonyl) Amino propyloxy-5-methoxy-2-aminobenzoyl]pyrrolidine-2-methanol 48

A mixture of the nitro compound 47 (5.5 g, 9.5 mmol) and SnCl$_2$/2H$_2$O (10.2 g, 45.4 mmol) in MeOH (100 mL) was heated at reflux and the progress of the reaction monitoring by TLC (95% CHCl$_3$/MeOH). After 2 hours excess MeOH was removed by evaporation under reduced pressure, the resulting residue was cooled (ice), and treated carefully with sat. aqueous NaHCO, (170 mL). The reaction mixture was diluted with EtOAc (170 mL) and after 16 hours stirring at room temperature the inorganic precipitate was removed by filtration through Celite. The organic layer was separated, washed with brine (150 mL), dried over MgSO$_4$ filtered and evaporated in vacuo to give a brown solid. Purification by flash column chromatography (95% g, 82%)

[α]=−78.6° (c=1.02, CHCl$_3$); mp=83–86° C.; $^1$H-NMR (CDCl$_3$, 270 MHz): δ 1.68–1.85 (m, 4H, H4+H3), 2.00–2.04 (m, 2H, H2'), 3.43–3.45 (m, 2H, R3'), 3.49–3.58 (m, 2H, H5), 3.67 (s, 3H, OCH$_3$), 3.72–3.78 (m, 2H, CH$_2$—OH), 4.04 (t, 2H, J=5.58 Hz, H1'), 4.22 (t, 1H, J=6.86 Hz, Fmoc CH), 4.41–4.44 (m, 3H, H2+Fmoc CH$_3$), 5.92 (br, 1H, NH), 6.23 (s, 1H, H3$_{arom}$), 6.71 (s, 1H, H6$_{arom}$), 7.27–7.41 (m, 4H, Fmoc$_{aryl}$), 7.62 (d, 2H, J=7.32 Hz, Fmoc$_{aryl}$), 7.75 (d, 2H, J=7.33 Hz, Fmoc$_{aryl}$); $^{13}$C-NMR (CDCl$_3$, 68.7 MHz): δ 24.9 (C4), 28.6 (C3), 29.1 (C2'), 39.5 (C3'), 47.3 (CH Fmoc), 51.0 (C5), 56.6 (OCH$_3$), 60.4 (C2), 61.1 (CH$_2$—OH), 66.4 (CH$_2$ Fmoc), 68.0 (C1'), 102.0 (C3$_{arom}$), 111.6 (C6$_{arom}$), 120.0, 125.1, 127.0 and 127.7 (CH Fmoc$_{aryl}$), 128.0 (C$_{arom}$), 137.8 (C$_{arom}$), 141.3 (C Fmoc$_{aryl}$), 144.0 (C Fmoc$_{aryl}$), 148.2 (C$_{arom}$), 150.8 (C$_{arom}$), 156.6 (NC=O$_{carbamata}$), 171.9 (C=O$_{amide}$); MS (FAB) m/z (relative intensity): 546 (M$^+$+1, 11), 445 (10), 191 (14), 179 (100), 166 (51), 102 (70); HRMS (FAB) exact mass calcd for C$_{31}$H$_{37}$N$_3$O$_6$ (M+H): m/e 546.2526 obsd m/e 546.2532; IR (Nujol) v: (cm$^{-1}$) 1698, 1622; 1588, 1506, 1476, 1404, 1228, 1173.

Synthesis of (2S) -N-[4- (N-9-fluorenylmethoxycarbonyl)amino propyloxy-5-methoxy-2-(N-resin-methoxybenzyloxycarbonyl) aminobenzoyl]pyrrolidine-2-methanol 49

The p-nitrophenyl carbonate Wang resin 31 (1 g, 0.54 mmol) was allowed to swell for 30 minutes in DCM/DMF (2:1, 10 mL) with gentle shaking in a round bottom flask equipped with a sintered glass filter tube. A solution of HOBt (0.22 g, 1.6 mmol), DIPEA (0.56 mL, 0.42 g, 3.2 mmol) and the amine 48 (1.47 g, 2.7 mmol) in DCM/DMF (2:1, 20 mL) was added to the swollen resin. The reaction mixture was shaken for 6 hours at room temperature and allowed to stand overnight, after this time the supernatant was removed by vacuum filtration using the sintered filter tube. The resin was washed four times with DCM, MeOH, and Et$_2$O for 2 minutes each. After this, the resin was dried in vacuo to afford the resin bound carbamate 49.

Synthesis of (11s, 11aS)-10-(N-resin-methoxybenzyloxycarbamate)-11-hvdroxy-8-(N-9-fluorenylmethoxycarbonyl)aminopropyloxy-7-methoxy-1,2,3,6,9,11a-hexahydro-5H-pyrrolo[2,1-c][1,4]benzodiazeipin-5-one 50

The carbamate bearing resin 49 (0.54 mmol) was allowed to swell for 30 minutes in DCM/DMF (2:1, 10 mL) with gentle shaking. A solution of the Dess-martin reagent (1.14 g, 2.7 mmol) in DCM/DMF (2:1, 20 mL) was added to the swollen resin. The reaction mixture was shaken for 2 hours at room temperature, after this time the supernatant was removed by vacuum filtration using the filter tube. The resin was washed four times with DCM, MeOH, and Et$_2$O for 2 minutes each. The resin was dried in vacuo to afford the resin bound carbinolamine 50.

Synthesis of (11aS) 8-(N-9-fluorenylmethoxycarbonyl)aminopropyloxy-7-methoxy-1,2,3,11a-tetrahydro-5H-pyrrolor[2,1-c][1,4]benzodiazeiin-5-one 51

The protected carbinolamine bound resin 50 (0.54 mmol) was suspended in TFA/DCM (1:1, 20 mL) and shaken for 2 hours at room temperature. After this time the supernatant was decanted by pressure and the resin was washed twice with DCM. The deprotection protocol was repeated once to ensure complete cleavage of the PBD from the resin. The combined organic solution was diluted with water and carefully neutralised with sat. aqueous NaHCO$_3$. The organic layer was separated, washed with H$_2$O (2×60 mL), brine (2×60 mL), dried over MgSO$_4$ and excess of solvent was removed by evaporation under reduced pressure. Purification by flash column chromatography (97% CHCl$_3$/MeOH) furnished the target compound 51 as a brown solid (67 mg, 24%) which was repeatedly evaporated in vacuo with CHCl$_3$ in an attempt to provide the N10-C11 imine form of the compound.

[α]$_D$=+397.5° (c=0.67, CHCl$_3$); $^1$H-NMR (CDCl$_3$, 270 MHz): δ 2.00–2.06 (m, 4H, H2+H1), 2.26–2.31 (m, 2H, H2'), 3.45–3.47 (m, 2H, H3'), 3.52–3.62 (m, 2H, H3), 3.80 (s, 3H, OCH$_3$), 3.91–4.24 (m, 4H, H11a+H1'+Fmoc CH), 4.43–4.46 (m, 2H, Fmoc CH$_2$), 5.93 (br, 1H, NH), 6.78 (s, 1H, H6), 7.26–7.41 (m, 4H, Fmoc$_{aryl}$), 7.5 (s, 1H, H9), 7.61 (d, 2H, J=7.14 Hz, Fmoc$_{aryl}$), 7.66 (d, 1H, J=4.39 Hz, H11$_{imine}$), 7.75 (d, 2H, J=7.33 Hz, Fmoc$_{aryl}$); $^{13}$C-NMR (CDCl$_3$, 68.7 MHz): δ 24.2 (C2), 29.0 (C1), 29.6 (C2'), 39.5 (C3'), 46.7 (C3), 47.4 (CH Fmoc), 53.7 (OCH$_3$), 56.0 (C11a), 66.3 (CH$_2$ Fmoc), 68.2 (C1'), 110.3 (C6), 111.4 (C9), 120.0 (C-H$_{aryl}$ Fmoc), 120.5 (C$_{arom}$), 125.1, 127.0, and 127.6 (C-H$_{aryl}$ Fmoc), 140.6 (C$_{arom}$), 141.3 (C$_{aryl}$ Fmoc), 144.0 (C$_{aryl}$ Fmoc), 147.7 (C$_{arom}$), 150.4 (C$_{arom}$), 156.6 (NC=O$_{carbamata}$), 162.6 (C11), 164.5 (C4$_{amide}$); IR (Nujol) v: (cm$^{-1}$) 3364, 1711, 1686, 1600, 1521, 1472, 1244, 1217, 1021, 740, 679.

EXAMPLE 10

Figure 12:
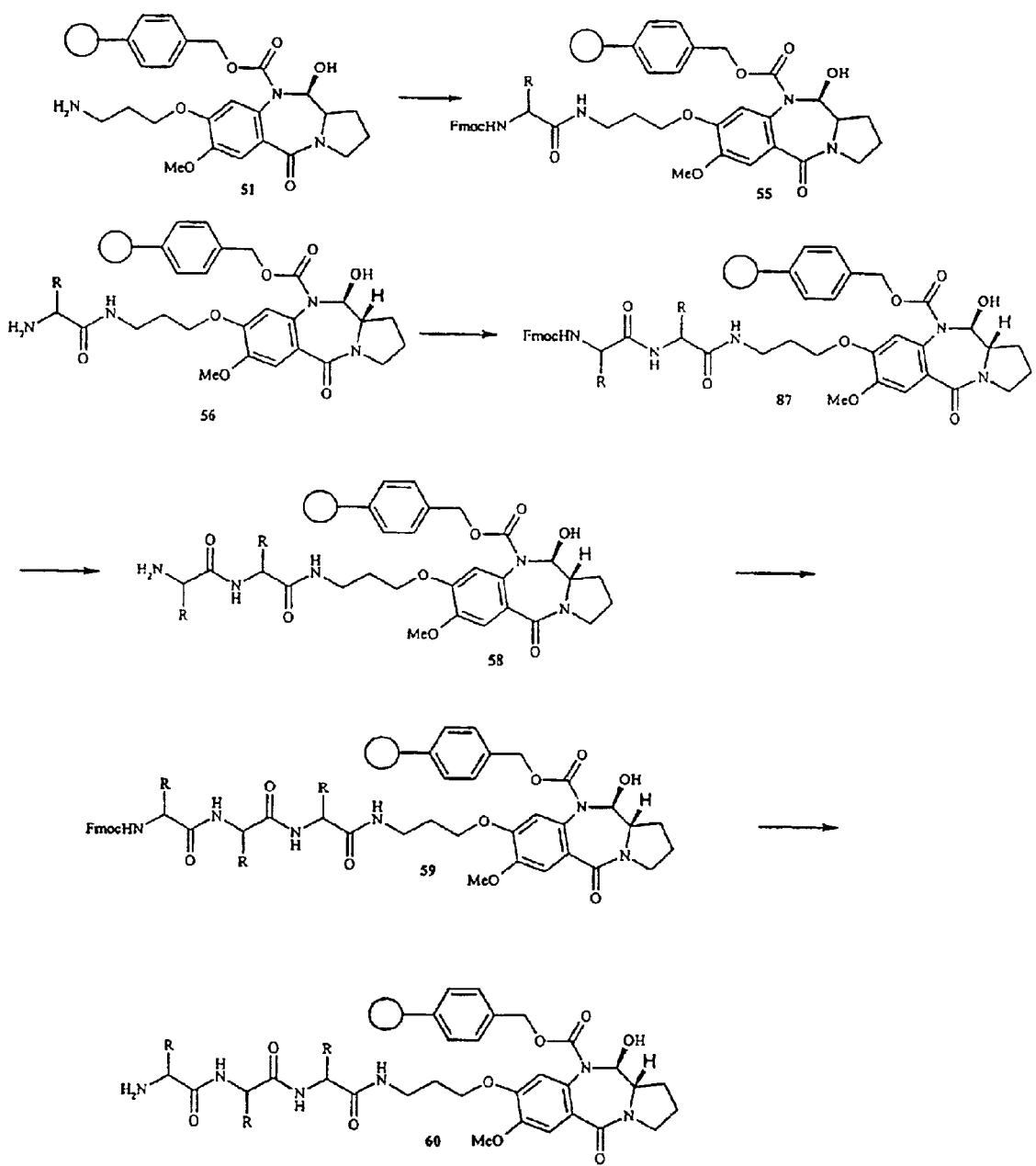

Synthesis of 27 Member Tripeptide PED Library 60 (FIG. 12)

A suspension of the amino PBD scaffold resin 30 (example 9)(0.45 mmol), in 2:1 DCE:DMF (30 mL) was evenly distributed between 27 Alltech tubes (1.5 mL volume). The process was repeated twice, excess solvent was removed by suction and the resin was rinsed with $CH_2Cl_2$ (2×5 mL) and dried in vacuo.

A solution of Fmoc-amino acid (0.05 mmol/tube) [Fmoc-alanine 15 mg/tube, Fmoc-glycine 14 mg/tube, Fmoc-phenylalanine 19 mg/tube], TBTU (15 mg, 0.05 mmol/tube) and DIPEA (8 mL, 0.05 mmol/tube) in DMF (500 mL) was added to resin 30 (0.017 mmol/tube) and allowed to shake for 16 hours. Resin 55 was filtered and rinsed with DMF (2×1 mL), $CH_2Cl_2$ (2×1 mL), MeOH (2×1 mL) and dried in vacuo.

The procedure was repeated once.

A solution of 20% piperidine in DMF (250 mL) was added to each tube and shaken for 2 hours. Resin 56 was filtered and rinsed with DMF (2×1 mL), $CH_2Cl_2$ (2×1 mL), MeOH (2×1 mL) and dried in vacuo. The procedure was repeated once.

The above coupling and deprotection protocols were repeated twice until the library of 27 tripeptides 60 was generated.

What is claimed is:

1. A compound of formula II:

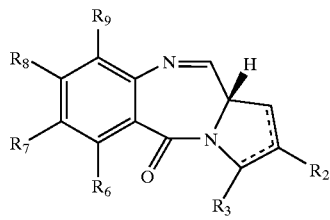

(II)

wherein $R_2$ and $R_3$ are independently selected from: H, R, OH, OR, =O, =CH—R, =$CH_2$, $CH_2$—$CO_2$ R , $CH_2$—$CO_2H$, $CH_2$-$SO_2R$, O—$SO_2R$, $CO_2R$, COR and CN, and there is optionally a double bond between C1 and C2 or C2 and C3;

$R_6$, $R_7$, $R_8$ and $R_9$ are independently selected from H, R, OH, OR, halo, nitro, amino, $Me_3Sn$; or $R_7$ and $R_8$ together form a group —O—$(CH_2)_p$—O—, where p is 1 or 2;

where R is a lower alkyl group having 1 to 10 carbon atoms, or an aralkyl group of up to 12 carbon atoms, whereof the alkyl group optionally contains one or more carbon—carbon double or triple bonds, which may form part of a conjugated system, or an aryl group of up to 12 carbon atoms; and is optionally substituted by one or more halo, hydroxy, amino, or nitro groups, and optionally contains one or more hetero atoms, which may form part of, or be, a functional group; except that one or more of $R_6$, $R_7$, and $R_8$ are independently X—Y—A—, where X is selected from —COZ', NHZ, SH, or OH, where Z is either H or a nitrogen protecting group, Z' is either OH or an acid protecting group, Y is a divalent group such that HY=R, and A is O.

2. A method of treating, neoplastic diseases, Alzheimer's disease, bacterial infections, parasitic infections or viral infections comprising administering a compound of formula II as defined in claim 1.

3. A pharmaceutical composition, comprising a compound of formula II as defined in claim 1, and a phaceutically acceptable carrier or diluent.

* * * * *